US009095587B2

(12) United States Patent
McCarthy et al.

(10) Patent No.: US 9,095,587 B2
(45) Date of Patent: Aug. 4, 2015

(54) METHODS AND COMPOSITIONS FOR IMPROVED NERVE CONDUCTION VELOCITY

(75) Inventors: Thomas David McCarthy, Malvern East (AU); Andrew Rainsford Bakeb, Highett (AU); Nancy Hancock, legal representative, Highett (AU)

(73) Assignee: Spinifex Pharmaceuticals Pty Ltd, Preston, Victoria (AU)

( * ) Notice: Subject to any disclaimer, the term of this patent is extended or adjusted under 35 U.S.C. 154(b) by 255 days.

(21) Appl. No.: 13/522,228

(22) PCT Filed: Jan. 19, 2011

(86) PCT No.: PCT/AU2011/000051
§ 371 (c)(1),
(2), (4) Date: Dec. 3, 2012

(87) PCT Pub. No.: WO2011/088504
PCT Pub. Date: Jul. 28, 2011

(65) Prior Publication Data
US 2013/0131103 A1     May 23, 2013

Related U.S. Application Data

(60) Provisional application No. 61/296,375, filed on Jan. 19, 2010.

(51) Int. Cl.
*A61K 31/472*     (2006.01)
*A61K 31/437*     (2006.01)
(Continued)

(52) U.S. Cl.
CPC .............. *A61K 31/472* (2013.01); *A61K 31/437* (2013.01); *A61K 31/4375* (2013.01); *A61K 31/522* (2013.01)

(58) Field of Classification Search
CPC ............ A61K 31/437; A61K 31/4375; A61K 31/472; A61K 31/522
USPC .................................................. 514/303, 307
See application file for complete search history.

(56) References Cited

U.S. PATENT DOCUMENTS

| 5,091,390 A | 2/1992 | Ardecky et al. |
| 5,236,934 A | 8/1993 | Van Atten et al. |
| 5,246,943 A | 9/1993 | Blankley et al. |

(Continued)

FOREIGN PATENT DOCUMENTS

| GB | 2337701 A | 12/1999 |
| WO | WO 93/20816 | 10/1993 |

(Continued)

OTHER PUBLICATIONS

Carbalho et al. (Muscle and Nerve, 2000, vol. 23, pp. 344-352).*
(Continued)

*Primary Examiner* — Savitha Rao
(74) *Attorney, Agent, or Firm* — Wolff IP a Prof. Corp; Jessica R. Wolff, Esq.

(57) ABSTRACT

The present invention provides methods and compositions for the effective treatment of impaired nerve signal conduction. Compositions including selective $AT_2$ receptor antagonists as active agents and methods of use in relation to improving nerve signal conduction or reversing impaired nerve signal conduction are described.

24 Claims, 5 Drawing Sheets

(51) Int. Cl.
A61K 31/4375 (2006.01)
A61K 31/522 (2006.01)

(56) References Cited

U.S. PATENT DOCUMENTS

| | | | |
|---|---|---|---|
| 7,795,275 | B2 | 9/2010 | Smith et al. |
| 7,828,840 | B2 | 11/2010 | Biggs et al. |
| 2006/0223741 | A1* | 10/2006 | Smith et al. ............ 514/2 |
| 2009/0177267 | A1 | 7/2009 | Biggs et al. |

FOREIGN PATENT DOCUMENTS

| | | |
|---|---|---|
| WO | WO 2006/066361 | 6/2006 |
| WO | WO 2007/106938 | 9/2007 |

OTHER PUBLICATIONS

Elsevier Science Daily article (Aug. 13, 2014, downloaded from the internet on Oct. 13, 2014, URL: http://www.sciencedaily.com/releases/2014/08/140813103451.htm).*

The Medline plus article from NIH (Nerve conduction velocity, Medline plus, May 28, 2013, downloaded from the internet on Oct. 13, 2014, URL: http://www.nlm.nih.gov/medlineplus/ency/article/003927.htm).*

European Supplemental Search Report Dated Jun. 25, 2013 for PCT/AU2011000051.

Coppey et al., "ACE Inhibitor or Angiotensin II Receptor Antagonist Attenuates Diabetic Neuropathy in Streptozotocin-induced Diabetic Rats," Diabetes, 55(2):341-348 (Feb. 2006).

Kasselman et al., "Local Administration of Angiotensin-2 Leads to Decreased Sensory Nerve Conduction Velocity in the Rat," Society for Neuroscience Abstract Viewer and Itinerary Planner, XP-002698686, Abstract for Presentation Nov. 17, 2008, 38th Annual Meeting of the Society for Neuroscience, Washington DC, USA, Nov. 15-19, 2008.

Blankley, et al., "Synthesis and Structure-Activity Relationships of a Novel Series of Non-Peptide Angiotensin II Receptor Binding Inhibitors Specific for the AT2 Subtype," J. Med. Chem., 1991, 34: 3248-3260.

Chiu, et al., "Identification of Angiotensin II Receptor Subtypes," Biochem. Biophys. Res. Commun., 1989, 165: 196-203.

Klutchko, et al., "Tetrahydroisoquinoline Derivatives With AT2-Specific Angiotensin II Receptor Binding Inhibitory Activity," Biorg. & Med. Chem. Lett., 1994, 4(1): 57-62.

Maxfield, et al., "Angiotensin II Receptor Blockade Improves Nerve Function, Modulates Nerve Blood Flow and Stimulates Endoneurial Angiogenesis in Spreptozotocin-Diabetic Rats and Nerve Function," Diabetologica, 1993, 36: 1230-1237.

Vanatten, et al., "A Novel Series of Selective, Non-Peptide Inhibitors of Angiotensin II Binding to the AT2 Site," J. Med. Chem., 1993, 36(25): 3985-3992.

PCT/AU2011/000051 International Preliminary Report on Patentability mailed on Aug. 2, 2012.

SIPO (People's Republic of China) Search Report Dated May 22, 2013 for Application No. 201180014579.1.

* cited by examiner

METHODS AND COMPOSITIONS FOR IMPROVED NERVE CONDUCTION VELOCITY

PRIORITY DATA AND INCORPORATION BY REFERENCE

This is a National Stage Application under 35 U.S.C §371 of International Application No. PCT/AU2011/000051, file Jan. 19, 2011, which claims the benefit of priority to U.S. Application Ser. No. 61/296,375, filed on Jan. 19, 2010, the entireties of which are hereby incorporated by reference.

FIELD OF THE INVENTION

The present invention relates generally to the use of selective angiotensin II type 2 ($AT_2$) receptor antagonists for improving nerve signal conduction or reversing impaired neuronal conduction velocity in a subject and the treatment or prophylaxis of conditions involving impaired nerve signal conduction.

BACKGROUND OF THE INVENTION

Nerve signal conduction velocity or nerve conduction velocity (NCV) is a characteristic of all nerve signal transmission. NCV is the rate at which a nerve impulse (signal) travels along a nerve or nerve fiber. It is typically measured in meters per second (m/s).

Impaired NCV is a common result of nerve damage. NCV is frequently involved in neuropathies, including, for example, peripheral neuropathies, carpel tunnel syndrome, ulnar neuropathy, Guillain-Barré Syndrome, facioscapulohumeral muscular dystrophy and spinal disc herneation. Impaired nerve conduction velocity can result in diminished reflex responses and altered peripheral sensation including paresthesia and in some cases pain.

Measurement of nerve conduction velocity in peripheral nerves has long been a valuable diagnostic tool in orthopedic surgery, neurology and other branches of medicine. A diminished velocity, amplitude or abnormal wave form suggests nerve damage. Such studies may also be used to indicate the development or onset of an abnormal condition. Such studies could, therefore, be used to permit prophylactic corrective action to be undertaken before permanent damage to the nerve occurs.

While there is no necessity to treat transient impairment of nerve conduction velocity, acute or chronic impairment may require treatment. At the present time, the symptoms of impairment are treated by attempting to determine the cause of the impairment and if there is treatment available, treating the cause. However, in some diseases or disorders, such as some neuropathies, no treatment may be available for treating underlying diseases or disorders.

Treatment to improve NCV or amelioration of its symptoms is desirable and can help prevent further nerve degeneration or further complicating conditions. For example, in diabetic patients, foot ischemia and infection are serious and even life-threatening occurrences. The most common causal pathway to diabetic foot ulceration has been identified as the combination of neuropathy (sensory loss), deformity (for example, prominent metatarsal heads), and trauma (for example, that caused by ill-fitting footwear). Peripheral neuropathy coupled with impaired sensation make the foot susceptible to trauma, ulceration, and infection. Diabetic neuropathy impairs the nerve axon reflex that depends on healthy C-fiber nociceptor function. This neuropathic condition also further compromises the vasodilatory response present in conditions of stress, such as injury or inflammation, in the diabetic neuropathic foot. This impairment may partially explain why some ulcers in the diabetic neuropathic foot are either slow to heal or fail to heal at all, despite successful lower-extremity revascularization. Clearly, a treatment that improves NCV can ameliorate the neuropathic conditions that are causal in the development of pernicious injury. Yet, despite the central role neuropathy may play in the development of pernicious debilitating conditions, neuropathy is one of the most difficult conditions to treat.

Angiotensin II type 1 ($AT_1$) receptor antagonists have been found to reverse impaired nerve conduction velocity in diabetic rats (WO 93/20816). Unfortunately, $AT_1$ receptor antagonists are known to have other biological effects, particularly as antihypertensive agents. Treatment of impaired NCV with $AT_1$ receptor antagonists can therefore precipitate undesirable or even proscriptive side effects. There is a need for other, more selective, or alternative treatments for impaired nerve conduction velocity that do not carry with them other biological effects.

Recently selective $AT_2$ receptor antagonists have been found to have analgesic effects in the treatment of neuropathic pain (WO 2006/066361), particularly in painful diabetic neuropathy (PDN). But not all neuropathic conditions that are associated with impaired nerve conduction velocity result in neuropathic pain. In some cases, the first symptom of a neuropathic condition is paresthesia, which may or may not be associated with pain. Further, techniques of NCV measurement now facilitate the early detection of impaired or sub-optimal nerve signal conduction velocities prior to the onset of more pernicious symptoms and conditions. There is therefore a need in some subjects to improve or increase nerve conduction velocities as a result of early diagnosis of impaired NCV.

Surprisingly, the present inventors have discovered that administration of selective $AT_2$ receptor antagonists can improve or increase nerve conduction velocities. Indeed, $AT_2$ receptor antagonists can be used to restore impaired nerve conduction velocity to normal levels, which can lead to relief of symptoms such as diminished reflex responses and altered peripheral sensation, including paresthesia, and the prevention of further nerve damage, which may prevent the development of neuropathic pain and further impairments arising from impaired nerve conduction velocities.

SUMMARY

The present disclosure includes methods of employing selective $AT_2$ receptor antagonists to increase or improve nerve conduction velocity in a subject. A particular method is a method for treating a subject in need of increased nerve conduction velocity (NCV), the method comprising providing to the subject a composition comprising an $AT_2$ receptor antagonist in an amount effective to increase NCV in the subject. Another method is a method of reversing impaired NCV, the method comprising providing to the subject a composition comprising an $AT_2$ receptor antagonist in an amount effective to reverse NCV in the subject.

Also disclosed is the use of an $AT_2$ receptor antagonist in the manufacture of a medicament for the treatment of a subject in need of increased nerve conduction velocity (NCV) or in need of reversing impaired NCV. In particular embodiments, the methods include use of an effective amount of at least one $AT_2$ receptor antagonist for the preparation of a pharmaceutical composition for achieving increased NCV or reversing NCV.

The disclosed methods of employing AT$_2$ receptor antagonists include methods to treat conditions or illnesses that involve impaired nerve conduction velocity or whose treatment may benefit from increased NCV. In particular embodiments the methods disclosed are part of a protocol for the treatment of a neuropathy, whether acquired or congenital.

Also disclosed is an AT$_2$ receptor antagonist for use in the treatment of a subject in need of increased nerve conduction velocity (NCV) or in need of reversing impaired NCV.

In particular embodiments, the subject has a neuropathic condition, especially a diabetic neuropathy. In particularly preferred embodiments the subject has a neuropathic condition but not a painful neuropathic condition.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the invention presented herein.

DETAILED DESCRIPTION

Figure 1:
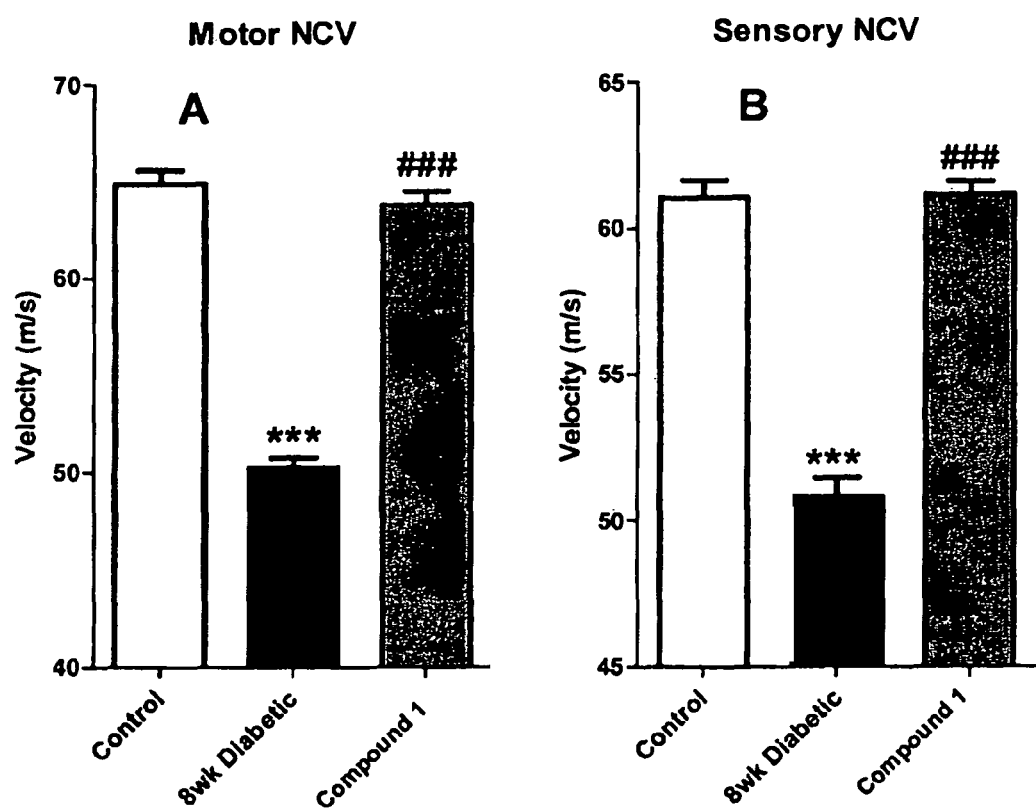
FIG. 1 is a graphical representation of the effects of diabetes and treatment of Compound 1 at an oral dose level of 1.043 mg/kg on (A) sciatic motor nerve conduction velocity (MNCV) and (B) saphenous sensory nerve conduction velocity (SNCV) for 14 days duration. Data are mean±SEM. ***, $P<0.001$, $<0.01$ vs nondiabetic control group; ###, $P<0.001$ treatment effect vs diabetic control group.

The following detailed descriptions of particular embodiments and examples are offered by way of illustration and not by way of limitation.

Unless contraindicated or noted otherwise, throughout this specification, the terms "a" and "an" mean one or more, the term "or" means and/or.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

I. NCV and Conditions Involving Impaired NCV

Nerve conduction velocity (NCV) is assessed by evaluating the electrical conduction of motor and sensory nerves in the body. Motor nerve conduction velocity measurements may be made by stimulating a peripheral nerve with an electrical impulse and measuring the time or latency from the stimulation until an action potential occurs in a muscle innervated by the nerve under examination. Measurements can be made by the use of surface electrodes positioned over the muscle that picks up the signals which are then amplified and displayed on a screen of a cathode ray tube or an oscilloscope. Sensory nerve conduction is assessed in a similar manner with stimulation of a peripheral nerve and recording at a sensory site such as a finger or paw pad. Measurements of the distance between the stimulus and response, which peak on the screen of the oscilloscope, are converted into latency times. The time taken is measured in milliseconds and is converted to a velocity (m/s) by taking into account the distance the impulse travelled. This technique is referred to as electromyography (EMG).

Established protocols for measurement of NCV include well known techniques to assess amplitude, latency, and wave forms generated by appropriate and specific stimulation of the nerve or nerves. In addition to NCV in m/s, indices of F-wave may be recorded or reported. Additional means for assessing impaired NCV include H-reflex studies, blink reflexes, and automated NCV testing machines. Assessment of blink reflexes can be important in the assessment of conditions involving the brainstem, or the $5^{th}$-$7^{th}$ cranial nerves. Abnormal latency of the blink reflex response may be indicative of NCV pathology in these regions.

These and related technologies are known in the art. For example, U.S. Pat. Nos. 4,291,705, 4,807,643, and 7,628,761 disclose methods and apparatus for performing conduction studies, the disclosures of which are hereby incorporated by reference.

By the phrases "impaired NCV" or "impaired nerve conduction velocity" and the like is meant any nerve conduction demonstrably abnormal in any one of the parameters assessed for normal nerve signal conduction. Whether the various parameters of NCV are normal is typically an assessment made by the relevant trained clinician. General background, terminology and procedures known to those in the art for evaluating NCV are described in "Proper performance and interpretation of electrodiagnostic studies" Muscle Nerve. (2006) 33(3):436-439 and "Electrodiagnostic medicine listing of sensory, motor, and mixed nerves." Appendix J of Current Procedural Terminology (CPT) 2007, authored by The American Association of Neuromuscular & Electrodiagnostic Medicine and published by the American Medical Association.

Impaired or abnormal nerve conduction velocity is a symptom of nerve dysfunction or damage and may be causal to or a symptom of a large number of diseases or disorders, particularly diseases or disorders that exhibit diminished reflex responses and altered peripheral sensation including paresthesia. As used herein, "paresthesia" refers to a sensation of tingling, prickling, weakness or numbness in a subject's skin. It is also known as "pins and needles" or a limb "falling asleep". Paresthesia may be transient, acute or chronic and may occur alone or be accompanied by other symptoms such as pain.

The term "pain" as used herein is given its common sense and includes an unpleasant sensory and emotional experience associated with actual or potential tissue damage, or described in terms of such damage and includes the more or less localized sensation of discomfort, distress, or agony, resulting from the stimulation of specialized nerve endings.

The methods of the invention may be useful in treating, preventing, alleviating, delaying or preventing the progression of diseases and disorders associated with impaired NCV including neuropathic conditions. There are many possible causes of neuropathy and it will be understood that the present invention contemplates the treatment or prevention of any neuropathic condition amenable to treatment by the compounds and methods disclosed regardless of the cause of the condition. In some embodiments, the neuropathic conditions are a result of diseases of the nerves (primary neuropathy) and neuropathy that is caused by systemic disease (secondary neuropathy) such as but not limited to: diabetic neuropathy; herpes zoster (shingles)-related neuropathy; uremia-associated neuropathy; amyloidosis neuropathy; HIV sensory neuropathies; hereditary motor and sensory neuropathies (HMSN); hereditary sensory neuropathies (HSNs); hereditary sensory and autonomic neuropathies; hereditary neuropathies with ulcero-mutilation; nitrofurantoin neuropathy; tumaculous neuropathy; neuropathy caused by nutritional deficiency and neuropathy caused by kidney failure. Other causes include repetitive activities such as typing or working on an assembly line, medications known to cause peripheral neuropathy such as several antiretroviral drugs [such as ddC (zalcitabine) and ddI (didanosine) and selected HIV protease inhibitors], antibiotics (such as metronidazole, an antibiotic used for Crohn's disease, isoniazid used for tuberculosis), gold compounds (used for rheumatoid arthritis), some chemotherapy drugs (such as vincristine and others) and many others. Chemical compounds are also known to cause peripheral neuropathy including alcohol, lead, arsenic, mercury and organophosphate pesticides. Some peripheral neuropathies are associated with infectious processes (such as Guillian-Barre syndrome). In certain embodiments, the neuropathic condition is a peripheral neuropathic condition, such as a diabetic neuropathy.

These are many types of diabetic neuropathy, some types include pain, such as painful diabetic neuropathy (PDN) whereas others occur without pain. The neuropathic condition may not include pain as a symptom.

The present invention is not for the purpose of providing analgesia for pain that is present, but is instead for improving the function of nerves whose function is impaired.

The term "analgesia" is used herein to describe states of reduced pain perception, including absence from pain sensations as well as states of reduced or absent sensitivity to noxious stimuli. Such states of reduced or absent pain perception are induced by the administration of a pain-controlling agent or agents and occur without loss of consciousness, as is commonly understood in the art. The term analgesia encompasses the term "antinociception", which is used in the art as a quantitative measure of analgesia or reduced pain sensitivity in animal models.

In some embodiments, the subject has symptoms of diminished reflex responses and altered peripheral sensation including paresthesia. In some embodiments, the disease or disorder involving impaired nerve conduction velocity is selected from a peripheral neuropathy, a compression neuropathy, an entrapment neuropathy, a neuropathy associated with a toxin, a disease or condition which includes diminished reflex responses and altered peripheral sensation including paresthesia as symptoms, Guillain-Barré Syndrome, facioscapulohumeral muscular dystrophy, or a condition resulting from nerve damage. In particular embodiments, the disease or condition is a diabetic neuropathy.

Further conditions involving impaired NCV and therefore amenable to treatment by the methods disclosed are identified by a subject presenting with indications of carpal tunnel syndromes (unilateral or bilateral), radiculopathy, mononeuropathy, polyneuropathy, myopathy, motor neuropathy, plexopathy, neuromuscular junction disfunction, tarsal tunnel syndromes (unilateral or bilateral), weakness, fatigue, cramps, or twitching, numbness or tingling (unilateral or bilateral).

II. Angiotensin II Type 2 Receptors

As used herein, the term "$AT_2$ receptor" means an angiotensin (Ang) II type 2 ($AT_2$) receptor polypeptide that can bind Ang II and/or one or more other ligands. The term "$AT_2$ receptor" encompasses vertebrate homologs of $AT_2$ receptor family members, including, but not limited to, mammalian, reptilian and avian homologs. Representative mammalian homologs of $AT_2$ receptor family members include, but are not limited to, murine and human homologs.

The $AT_2$ receptor is a subtype of angiotensin II receptors, and is distinct from the $AT_1$ receptor. In contrast to the current knowledge of $AT_2$ receptors, there are a number of biological activities associated ascribed to $AT_1$ receptors. Indeed, most of the known physiologic actions of angiotensin II are thought to be mediated through the stimulation of $AT_1$ receptors and antagonism of $AT_1$ receptors is a common treatment for hypertension and congestive heart failure. At present, no commercial drugs specifically target the $AT_2$ receptor and very few physiological roles have been ascribed to it in mammals.

III. Selective Angiotensin II Type 2 Antagonist Compounds

Angiotensin II Type 2 ($AT_2$) antagonists are antagonists to one of the two main subtypes of angiotensin II receptors, namely the angiotensin II type 2 receptor (A. T. Chiu et al., Biochem. Biophys. Res. Commun. 165:196-203 (1989)). WO 2006/066361 describes the use of $AT_2$ receptor antagonists as analgesics for the relief of neuropathic pain. U.S. Patent Publication number 20090177267 describes medical devices for the administration of $AT_2$ receptor antagonists in the treatment of vascular disease, especially abdominal aortic aneurysm.

As used herein, the term "$AT_2$ antagonist" means an agent or a compound or plurality of compounds, chemical compositions that decreases, inhibits, or modulates the biological activity of an $AT_2$ receptor polypeptide. $AT_2$ receptor antagonists may be any molecule or active compound that selectively binds to the $AT_2$ receptor subtype and that suitably modulates signaling through this receptor. The compounds include pharmaceutically compatible salts of the molecule or active compound. This category includes compounds showing differing structural features.

$AT_2$ receptor antagonist may be selected from compounds disclosed and described in U.S. Pat. No. 7,828,840, which is incorporated by reference herein in its entirety. Preferred embodiments may select compounds from those listed and described in International patent publication number WO 2006/066361, which is incorporated by reference herein in its entirety.

The compounds employed within the present methods are selective $AT_2$ receptor antagonists. Selective $AT_2$ receptor antagonists are typically compounds that have an $IC_{50}$ at the $AT_2$ receptor of ≤100 nM and an $IC_{50}$ at the $AT_1$ receptor of ≥100,000 nM (10 μM) using the assay methodology described herein.

In especially preferred embodiments, the selective $AT_2$ receptor antagonists useful in these methods are compounds of formula (I):

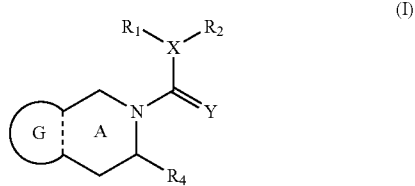

(I)

wherein
$R_1$ and $R_2$ are independently selected from hydrogen, phenyl, benzyl, $C_1$-$C_6$ alkyl, $C_3$-$C_6$ cycloalkyl and heteroaryl, provided that $R_1$ and $R_2$ are not both hydrogen;
$R_4$ is selected from a carboxylic acid, sulfate, phosphate, sulphonamide, phosphonamide and amide;
X is selected from CH, N, O and S provided that when X is O or S, one of $R_1$ and $R_2$ is absent;
Y is selected from S, O and N—$R_3$ wherein $R_3$ is selected from hydrogen, $C_{1-6}$ alkyl, aryl, —$C_1$-$C_4$ alkylaryl, —OH or —$NH_2$;
G is a 5 or 6 membered aromatic, heterocyclic or heteroaryl ring selected from:

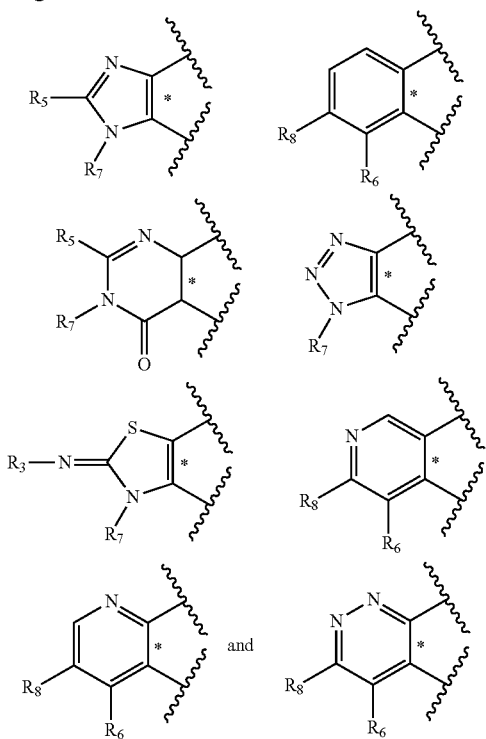

wherein the symbol "*" indicates the bond shared between the fused rings A and G;
$R_5$ is selected from hydrogen, $C_1$-$C_6$ alkyl, phenyl and $C_1$-$C_6$ alkoxy, $R_6$ and $R_8$ are independently, selected from hydrogen, $C_1$-$C_6$ alkyl, $C_1$-$C_6$ alkoxy, phenyl, benzyl, phenoxy, benzyloxy, benzylamino, biphenyl, biphenyloxy, naphthyl and naphthyloxy; provided that $R_6$ and $R_8$ are not both hydrogen; and
$R_7$ is selected from phenyl, benzyl, biphenyl, biphenylmethyl, naphthyl and naphthylmethyl;
wherein each alkyl, alkoxy, aryl, cycloalkyl, aryloxy, arylalkyl, arylalkyloxy and heteroaryl group is optionally substituted;
or a pharmaceutically acceptable salt thereof.

While not being bound by theory, it is believed that the selective and active functionality of the $AT_2$ receptor antagonists of Formula (I) employed by the methods disclosed herein owe their selectivity for and activity with the $AT_2$ receptor through the particular pharmacophore described by Formula (I). The relationship of structure and the effects of alternative substituents within Formula (I) are known. For example, see: Klutchko et al., (1994) Bioorganic & Medicinal Chemistry Letters 4(1):57-62; Blankley et al. (1991) J. Med. Chem. 34:3248-3260; and VanAtten et al. (1993) J. Med. Chem. 36(25):3985-3992. It is therefore understood that all compounds within the confines of Formula (I) will predictably share the fundamental selectivity and activity required for use within the methods disclosed through the shared pharmacophore described in Formula (I).

It is nevertheless specifically contemplated that any particular compound discussed herein may, in certain embodiments, be excluded from a genus of compounds or generic formula described herein.

In particular embodiments, the compound of formula (I) has one or more of the following features:
$R_1$ and $R_2$ are independently selected from hydrogen, optionally substituted phenyl and optionally substituted benzyl, provided that both $R_1$ and $R_2$ are not hydrogen, especially where at least one of $R_1$ and $R_2$ is optionally substituted phenyl, more especially where both $R_1$ and $R_2$ are optionally substituted phenyl, most especially where both $R_1$ and $R_2$ are unsubstituted phenyl;
$R_4$ is a carboxylic acid, especially a S-carboxylic acid;
X is CH or N, especially CH;
Y is oxygen or sulfur, especially oxygen,
G is

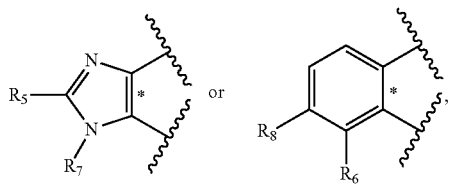

especially

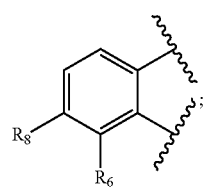

$R_5$ is hydrogen or $C_1$-$C_4$ alkyl, especially hydrogen;
$R_6$ is $C_1$-$C_6$ alkoxy, optionally substituted phenyloxy, optionally substituted benzyloxy, or optionally substituted biphenyloxy, especially optionally substituted phenoxy or optionally substituted benzyloxy, more especially unsubstituted benzyloxy;

$R_7$ is optionally substituted benzyl, optionally substituted biphenylmethyl and optionally substituted naphthylmethyl, especially optionally substituted benzyl, more especially benzyl substituted in the 3 and 4 position with substituents independently selected from methyl, methoxy, —$NH_2$, —$NHCH_3$ or —$N(CH_3)_2$;

$R_8$ is hydrogen, optionally substituted $C_1$-$C_6$ alkyl, or optionally substituted $C_1$-$C_6$ alkoxy, especially $C_1$-$C_6$ alkoxy, more especially methoxy.

In some embodiments, the compound of formula (I) is a compound of formula (II):

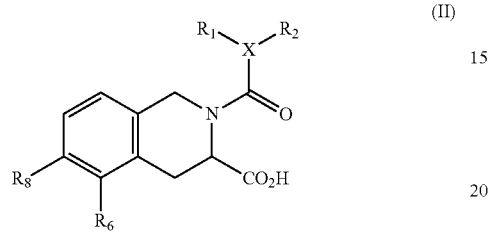
(II)

where $R_1$, $R_2$, $R_6$, $R_8$ and X are as defined for formula (I).

In some embodiments, the compound of formula (I) is a compound of formula (IIA):

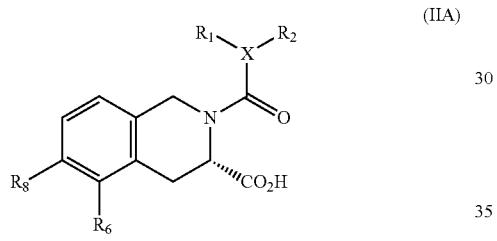
(IIA)

wherein $R_1$, $R_2$, $R_6$, $R_8$ and X are as defined for formula (I).

In particular embodiments, the compound of formula (II) or (IIA) is 2-(diphenylacetyl)-5-benzyloxy-6-methoxy-1,2,3,4-tetrahydroisoquinoline-3-carboxylic acid or an enantiomer thereof, especially S-2-(diphenylacetyl)-5-benzyloxy-6-methoxy-1,2,3,4-tetrahydroisoquinoline-3-carboxylic acid (Compound 1). Exemplary compound 1 is also identified as the S-enantiomer of PD 126055, (S)-2-(diphenylacetyl)-1,2,3,4-tetrahydro-6-methoxy-5-(phenylmethoxy)-3-isoquinoline carboxylic acid, and with reference to the following formula:

Compound 1
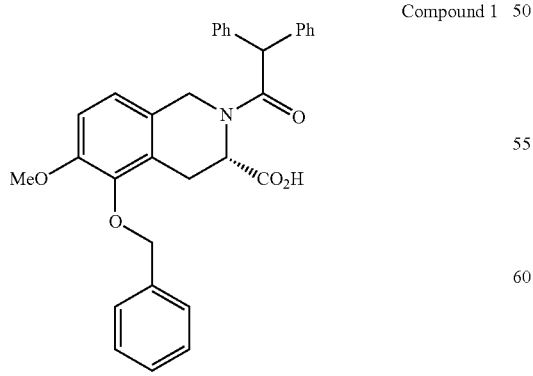

In some embodiments the compound of formula (I) is a compound of formula (III):

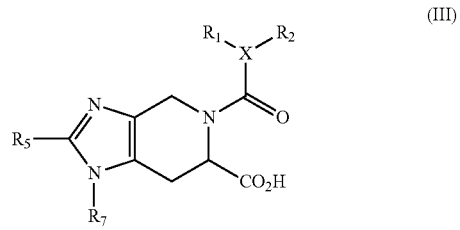
(III)

wherein $R_1$, $R_2$, $R_5$, $R_7$ and X are as defined for formula (I); especially a compound of formula (IIIA):

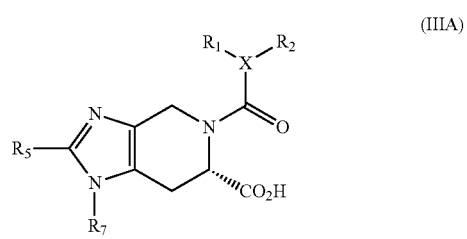
(IIIA)

wherein $R_1$, $R_2$, $R_5$, $R_7$ and X are as defined for formula (III).

In a particular embodiment the compound of formula (III) or (IIIA) is:
1-[[4-(dimethylamino)-3-methylphenyl]methyl]-5-diphenylacetyl-4,5,6,7-tetrahydro-1H-imidazo-[4,5c]pyridine-6-carboxylic acid or an enantiomer thereof, especially S-1-[[4-(dimethylamino)-3-methylphenyl]methyl]-5-diphenylacetyl-4,5,6,7-tetrahydro-1H-imidazo-[4,5c]pyridine-6-carboxylic acid (Compound 2) with reference to the formula:

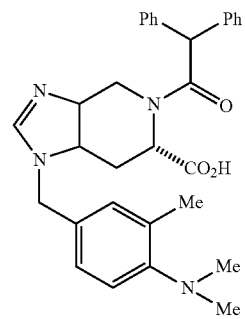 [SMILES: Cc1cc(CN2C=NC3CN(C(=O)C(c4ccccc4)c4ccccc4)[C@H](C(=O)O)CC32)ccc1N(C)C]

In a further particular embodiment the compound of formula (III) or (IIIA) is:
1-[[4-methoxy-3-methylphenyl]methyl]-5-diphenylacetyl-4,5,6,7-tetrahydro-1H-imidazo-[4,5c]pyridine-6-carboxylic acid; or an enantiomer thereof, especially S-1-[[4-methoxy-3-methylphenyl]methyl]-5-diphenylacetyl-4,5,6,7-tetrahydro-1H-imidazo-[4,5c]pyridine-6-carboxylic acid (Compound 3), with reference to the formula:

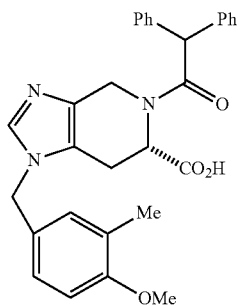

Compound 3

As used herein, "alkyl" is intended to include both branched and straight-chain saturated aliphatic hydrocarbon group containing from 1 to 10 carbon atoms and may have a specified number of carbon atoms. For example, $C_1$-$C_6$, as in "$C_1$-$C_6$alkyl" is defined to include groups having 1, 2, 3, 4, 5 or 6 carbons in linear or branched arrangement. For example, "$C_1$-$C_6$alkyl" specifically includes, but is not limited to, methyl, ethyl, n-propyl, i-propyl, n-butyl, t-butyl, i-butyl, pentyl or hexyl.

The term "alkenyl", unless otherwise indicated, refers to a hydrocarbon radical, straight or branched, containing from 2 to 10 carbon atoms and at least one carbon to carbon double bond. Thus, "$C_2$-$C_6$alkenyl" means an alkenyl radical having from 2 to 6 carbon atoms and the double bond may be between any two adjacent carbon atoms in the chain. Alkenyl groups include, but are not limited to, ethenyl, prop-1-enyl, prop-2-enyl, butenyl, pentenyl, hexenyl and 2-methylbutenyl.

The term "alkynyl" refers to a hydrocarbon radical, straight or branched, containing from 2 to 10 carbon atoms and at least one carbon to carbon triple bond. Thus, "$C_2$-$C_6$alkynyl" means an alkynyl radical having from 2 to 6 carbon atoms and the triple bond may be between any two adjacent carbon atoms in the chain. Alkynyl groups include, but are not limited to, ethynyl, propynyl, butynyl, 3-methylbutynyl and so on.

The term "cycloalkyl" or "aliphatic ring" means a monocyclic saturated aliphatic hydrocarbon group and may have a specified number of carbon atoms in the ring, such as $C_3$ to $C_7$. For example, "cycloalkyl" includes, but is not limited to, cyclopropyl, cyclopropyl, cyclobutyl, cyclopentyl, cyclohexyl and cycloheptyl.

"Alkoxy" represents either a non-cyclic or cyclic (cycloalkyl) alkyl group attached through an oxygen bridge. "Alkoxy" therefore encompasses the definitions of alkyl and cycloalkyl above. For example, alkoxy groups include but are not limited to methoxy, ethoxy, n-propyloxy, i-propyloxy, cyclopentyloxy and cyclohexyloxy.

As used herein, "aromatic" or "aryl" is intended to mean any stable monocyclic or bicyclic carbon ring of up to 7 atoms in each ring, wherein at least one ring is aromatic. Examples of such aryl groups include, but are not limited to, phenyl, naphthyl, tetrahydronaphthyl, indanyl, biphenyl, phenanthryl, anthryl or acenaphthyl.

"Alkylaryl" means alkyl as defined above which is substituted with an aryl group as defined above, for example, —$CH_2$phenyl (benzyl), —$(CH_2)_2$phenyl (phenylethyl), —$(CH_2)_3$phenyl, —$CH_2CH(CH_3)CH_2$phenyl, —$CH_2$naphthyl (naphthylmethyl), —$CH_2CH_2$naphthyl (naphthylethyl), —$CH_2$biphenyl (biphenylmethyl) and the like.

"Aryloxy" unless otherwise indicated represents an aryl group attached through an oxygen bridge. Examples of aryloxy groups include —Ophenyl (phenoxy), —Ophenyl-phenyl (biphenyloxy) and —Onaphthyl (naphthyloxy).

The term "heterocycle", "heteroaliphatic" or "heterocyclyl" as used herein is intended to mean a 5- to 10-membered nonaromatic heterocycle, which may be saturated or unsaturated, containing from 1 to 4 heteroatoms selected from the group consisting of O, N and S, and includes bicyclic groups. The term heterocyclic includes the N-oxide derivative of any nitrogen containing heterocycle.

The term "heteroaryl" or "heteroaromatic," as used herein, represents a stable monocyclic or bicyclic ring of up to 7 atoms in each ring, wherein at least one ring is aromatic and contains from 1 to 4 heteroatoms selected from the group consisting of O, N and S. As with the definition of heterocycle, "heteroaryl" is also understood to include the N-oxide derivative of any nitrogen-containing heteroaryl.

Examples of "heteroaryl" and "heterocyclyl" include, but are not limited to, the following: acridinyl, benzoimidazolyl, benzofuranyl, benzofurazanyl, benzopyrazolyl, benzotriazolyl, benzothienyl, benzothiophenyl, benzoxazolyl, carbazolyl, carbolinyl, cinnolinyl, furanyl, imidazoyl, indolinyl, indolyl, indolazinyl, indazolyl, isobenzofuranyl, isoindolyl, isoquinolyl, isoquinolinyl, isothiazolyl, isoxazolyl, naphthpyridinyl, oxadiazolyl, oxazolyl, oxazoline, isoxazoline, oxetanyl, pyridinyl, pyranyl, pyrazinyl, pyrazolyl, pyridazinyl, pyridopyridinyl, pyridazinyl, pyridyl, pyrimidinyl, pyrrolyl, quinolinyl, quinazolinyl, quinolyl, quinoxalinyl, tetrahydropyranyl, tetrahydroquinolinyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

The term "optionally substituted" as used herein means that a group may be unsubstituted or may be further substituted by one or more additional substituents. Examples of additional substituents include —$C_1$-$C_{10}$alkyl, —$C_2$-$C_{10}$alkenyl, —$C_2$-$C_{10}$alkynyl, —$C_3$-$C_7$cycloalkyl, aryl, —$C_1$-$C_4$alkylaryl, heterocyclyl, heteroaryl, —$C_1$-$C_4$perfluoroalkyl, —OH, —SH, —CN, —$NO_2$, halo (F, Cl, Br, I), $C_1$-$C_{10}$alkoxy-, —$C_1$-$C_4$alkylhalo, —$C_1$-$C_4$alkylOH, —$C_1$-$C_4$alkylSH, —$NH_2$, —NH($C_1$-$C_4$alkyl), —N($C_1$-$C_4$alkyl)$_2$, —NHaryl, —N(aryl)$_2$, aryloxy-, arylC$_1$-$C_4$alkyloxy-, formyl, $C_1$-$C_{10}$alkylC(O)—, $C_1$-$C_{10}$alkoxyC(O)—, —$PO_3H_2$, —$CO_2H$, —$CONHSO_2R_{10}$, —$CONHSO_2NHR_{10}$, —$NHCONHSO_2R_{10}$, —$NHSO_2R_{10}$, —$NHSO_2NHCOR_{10}$, —$SO_2NHR_{10}$, —$SO_2NHCOR_{10}$, —$SONHCONHR_{10}$, —$SO_2NHCO_2R_{10}$, —$CO_2R_{10}$, —$CONH_2$, —NHCHO, —$COC_1$-$C_4$perfluoroalkyl, —$SOC_1$-$C_4$ perfluoroalkyl and —$SO_2C_1$-$C_4$perfluoroalkyl, wherein $R_{10}$ is selected from hydrogen, —$C_1$-$C_4$alkyl, aryl, —$C_1$-$C_4$alkylaryl, cycloalkyl, heterocyclyl and heteroaryl.

As used herein the term "perfluoroalkyl" refers to an alkyl group in which all hydrogen atoms have been replaced with fluorine atoms. Examples include, but are not limited to, —$CF_3$, —$CF_2CF_3$, —$CF_2CF_2CF_3$ and —$CF(CF_3)_2$.

It will be recognized that the compounds described herein may possess asymmetric centres and are therefore capable of existing in stereoisomeric form. The methods also encompass the use of compounds in substantially pure stereoisomeric form at one or more asymmetric centres, for example: greater than about 90% ee, such as 95%, 97% or 99% ee. The invention also encompasses mixtures of stereoisomers, including racemic mixtures.

The terms "pharmaceutically compatible salt" and "pharmaceutically acceptable salt" are used interchangeably to refer to a salt which is toxicologically safe for human and animal administration. This salt may be selected from a group including hydrochlorides, hydrobromides, hydroiodides, sulfates, bisulfates, nitrates, citrates, tartrates, bitartrates, phosphates, malates, maleates, napsylates, fumarates, succinates, acetates, terephthalates, pamoates and pectinates. Base salts include those formed with pharmaceutical cations including sodium, potassium, lithium, calcium, magnesium, ammonium and dialkylammonium. Pharmaceutically acceptable salts include both the metallic (inorganic) salts and organic salts; a non-exhaustive list of which is given in Remington's Pharmaceutical Sciences, 18$^{th}$ Ed. Mack Printing Company, 1990. It is well known to one skilled in the art that an appropriate salt form is chosen based on physical and chemical stability, flowability, hydroscopicity and solubility.

IV. Methods of Treatment to Improve NCV

As used herein, "subject" or "individual" or "patient" refers to any subject for whom or which therapy is desired, and generally refers to the recipient of the therapy to be practiced according to the invention. The subject can be any vertebrate, but will preferably be a mammal. If a mammal, the subject will preferably be a human, but may also be a domestic livestock, laboratory subject or pet animal.

"Treatment" or "treating" as used herein means any therapeutic intervention in a subject, usually a mammalian subject, generally a human subject, including: (i) relief, that is, causing an increase in NCV in the subject; (ii) the regression of symptoms, for example, causing relief from symptoms arising from or associated with impaired NCV or conditions involving impaired NCV; (iii) prevention, that is, causing the symptoms not to develop, for example, preventing progression of symptoms or other conditions involving impaired NCV to a harmful state; or (iv) inhibition, that is, arresting the development or further development of symptoms, for example, mitigating or completely inhibiting active (ongoing) deterioration. Treatment includes prophylaxis and therapy.

As used herein "improvement of NCV" or "to improve NCV" refers to a change in NCV measured parameters or associated or indicative symptoms towards a therapeutically desired end state. As contemplated and used herein, such an improvement does not necessarily imply or require complete elimination of symptoms or a return to normal condition, nor even achieving a therapeutically desired state of the subject treated. Rather, improvement includes any measurable change towards a desired state. Similarly, "increased NCV" as used herein refers to any measurable increase in the rate at which nerve signals are conducted or any measurable improvement in other parameters or symptoms.

Treatment of impaired NCV to result in increased or improved NCV can itself be prophylactic of more pernicious conditions arising from the presence of impaired NCV. For example, impaired sensory perception in limbs of diabetic subjects may result in injuries, some debilitating, that may be prevented by improving the NCV of the subject to counter the impairment of sensory perception.

Prophylaxis or therapy can be accomplished by a single direct administration at a single time point or multiple time points. Administration can also be delivered to a single or to multiple sites. In certain embodiments, an $AT_2$ receptor antagonist may be given to a subject who has not responded, or who has negatively responded, to the administration of conventional therapies. Similarly, in certain embodiments, an $AT_2$ receptor antagonist may be given to a subject who has been identified as susceptible to undesired or proscriptive side effects of other treatments of impaired NCV.

By "effective amount," "therapeutic amount," or "therapeutically effective amount," in the context of treating or preventing a condition, is meant the delivery of that amount of active compound to an individual in need of such treatment or prophylaxis, either in a single dose or as part of a series, that is effective for the prevention of incurring a symptom, holding in check such symptoms, and/or treating existing symptoms, of that condition. In particular, in the context of the present methods, an effective amount means the delivery of an amount of $AT_2$ receptor antagonist effective to result in the increase of measured NCV. In this context, an increase in measured NCV may be recognized by direct or comparative measurement of NCV or through assessment of symptoms or conditions correlative or indicative of improved or increased NCV.

The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials but does not cause undesirable or intolerable side effects. In general, the $AT_2$ receptor antagonist (or pharmaceutically acceptable salt thereof) will be administered to a man so that, for example, a daily oral dose of up to 50 mg/kg body weight, especially up to 10 mg/kg or a daily parenteral dose of up to 5 mg/kg body weight, especially up to 1 mg/kg, is given, in divided doses if necessary.

In other non-limiting examples, a dose may also comprise from about 1 microgram/kg/body weight, about 5 microgram/kg/body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg/body weight, about 5 milligram/kg body weight, about 10 milligram/kg/body weight, about 20 milligram/kg body weight, about 50 milligram/kg body weight per administration, and any range derivable therein. In non-limiting examples of a derivable range from the numbers listed herein, a range of about 5 mg/kg body weight to about 50 mg/kg body weight, about 5 microgram/kg/body weight to about 500 milligram/kg body weight, etc., can be administered.

The effective amount for any particular subject or class of subjects or taxon may be conveniently determined through routine trials wherein NCV is measured or a correlated symptom assessed prior to treatment, an initial dose of up to 50 mg/kg body weight, especially up to 10 mg/kg or a daily parenteral dose of up to 5 mg/kg body weight, especially up to 1 mg/kg, is given, followed by subsequent measurement of NCV or assessment of a correlated symptom or condition. Adjustments in the dose or doses or dose regime may be made based upon the degree of improvement or successful result achieved with the initial dose. Further monitoring of improved symptoms or increased NCV may be ongoing and doses adjusted accordingly. It may be advisable to administer the composition comprising an $AT_2$ receptor antagonist in a low dosage, then increase the dosage as needed to achieve the desired therapeutic goal. Increasing amounts of an $AT_2$ receptor antagonist can be administered until an increase in NCV is detected or a reduction or mitigation of related symptoms is achieved.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

Similarly, the choice of $AT_2$ receptor antagonist for a particular subject or therapeutic regime may depend upon the health and physical condition of the individual to be treated, the taxonomic group of individual to be treated, the formulation of the composition, the assessment of the medical situation, and other relevant factors. In making such choices reference may be made to known relationships between variations in structure and substituents of the compounds of formula (I) in order to achieve a desired outcome in any particular therapeutic setting or formulation. The assessment of the relevant factors for any particular $AT_2$ receptor antagonist for a particular subject or therapeutic regime is well within the scope of routine experimentation in the art.

V. Pharmaceutical Formulations

Certain of the methods set forth herein pertain to methods involving the administration of a pharmaceutically and/or therapeutically effective amount of an $AT_2$ receptor antagonist for purposes of increasing NCV. An $AT_2$ receptor antagonist may be administered by any conventional methods available for use in conjunction with pharmaceuticals, either as an individual therapeutically active ingredient or in a combination of therapeutically active ingredients. An $AT_2$ receptor antagonist may be administered alone, but will generally be administered with a pharmaceutically acceptable carrier selected on the basis of the chosen route of administration and standard pharmaceutical practice.

An $AT_2$ receptor antagonist may be extensively purified and/or dialyzed to remove undesired small molecular weight molecules and/or lyophilized for more ready formulation into a desired vehicle, where appropriate. Such methods are well-known in the art. The active compounds will then generally be formulated for administration by any known route, such as oral or parenteral administration. Methods of administration are discussed in greater detail below.

Any compound discussed herein is contemplated as comprised in a pharmaceutical composition. Pharmaceutical compositions of the present invention comprise an effective amount of one or more active compounds (for example, an $AT_2$ receptor antagonist) or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one active compound or additional active ingredient will be known to those of skill in the art in light of the present disclosure, as exemplified by Remington's Pharmaceutical Sciences, 18$^{th}$ Ed. Mack Printing Company, 1990, incorporated herein by reference.

Moreover, for animal (for example, human) administration, it will be understood that preparations should meet sterility, pyrogenicity, general safety and purity standards as required by the U.S. FDA's Center of Drug Evaluation and Research.

As used herein, "pharmaceutically acceptable carrier" includes any and all solvents, dispersion media, coatings, surfactants, antioxidants, preservatives (for example, antibacterial agents, antifungal agents), isotonic agents, absorption delaying agents, salts, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it needs to be sterile for such routes of administration as injection. The present invention can be administered intravenously, intradermally, intraarterially, intraperitoneally, intralesionally, intracranially, intraarticularly, intraprostatically, intrapleurally, intratracheally, intranasally, intravitreally, intravaginally, intrarectally, topically, intramuscularly, subcutaneously, subconjunctival, intravesicularly, mucosally, buccally, transdermally, intrapericardially, intraumbilically, intraocularally, orally, locally, via inhalation (for example, aerosol inhalation), via injection, via infusion, via continuous infusion, via localized perfusion bathing target cells directly, via a catheter, via eye or ear drops, via a lavage, in cremes, in lipid compositions (for example, liposomes), or by other method or any combination of the foregoing as would be known to one of ordinary skill in the art (see, for example, Remington's Pharmaceutical Sciences, 1990).

In certain embodiments, pharmaceutical compositions may comprise, for example, at least about 0.1% of a compound of the present invention. In other embodiments, an $AT_2$ receptor antagonist may comprise between about 2% to about 75% of the weight of the unit, or between about 25% to about 60%, for example, and any range derivable therein.

In embodiments where the composition is in a liquid form, a carrier can be a solvent or dispersion medium comprising but not limited to, water, ethanol, polyol (for example, glycerol, propylene glycol, liquid polyethylene glycol, etc.), lipids (for example, triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In certain embodiments the active compound is prepared for administration by such routes as oral ingestion. In these embodiments, the solid composition may comprise, for example, solutions, suspensions, emulsions, tablets, pills, capsules (for example, hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

Dosage formulations of the present pharmaceutical compositions can be prepared by combining them with a pharmaceutically acceptable carrier, such as a slow release agent, to make either immediate or slow release formulations as is well known in the art. Such pharmaceutically acceptable carriers may be either solid or liquid in form such as, for example, cornstarch, lactose, sucrose, peanut oil, olive oil, sesame oil, propylene glycol and water. If a solid carrier is used, the dosage formulation of the present pharmaceutical compositions may be in, for example, powder, troche, or lozenges form. If a liquid carrier is used, the dosage formulation of the present pharmaceutical compositions may be in, for example, soft gelatin capsule, syrup liquid suspension, emulsion, or solution form. The dosage formulations may also contain adjuvants, such as preserving, stabilizing, wetting or emulsifying agents, or solution promoters. Immediate and slow release formulations are well known in the art.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Certain coating materials are those which dissolve at about or at least about a pH of 5 or above, such as at about pH 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0 or above, such as pH of about 6.5 or above. Such coatings therefore only begin to dissolve when they have left the stomach and entered the small intestine. Accordingly, these coatings may be considered enteric coatings. A thick layer of coating is provided which will dissolve in minutes to hours, thereby allowing the capsule underneath to breakup only when it has reached the terminal ileum or the colon. Such a coating can be made from a variety of polymers such as cellulose acetate trimellitate (CAT), hydroxypropylmethyl cellulose phthalate (HPMCP), polyvinyl acetate phthalate (PVAP), cellulose acetate phthalate (CAP) and shellac. For coatings of cellulose esters, a thickness of 200-250 micrometers would be suitable.

Non-limiting exemplary coating materials are methyl methacrylates or copolymers of methacrylic acid and methyl methacrylate. Such materials are available as polymers (Rohm Pharma, Darmstadt, Germany). Eudragits are copolymers of methacrylic acid and methyl methacrylate (Rohm Pharma, Darmstadt, Germany). It is specifically contemplated that compounds of the present invention may be incorporated into the polymers that act as carriers that are nonabsorbable. Compounds of the present invention may be, for example, covalently bonded to such polymers. Such polymers may be, for example, the polymers mentioned above and/or the polymer tails and polymer backbones discussed herein.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsions, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

A composition comprising an $AT_2$ receptor antagonist may be formulated for topical administration, for example, in a cream as mentioned, or in an ointment, salve, spray, gel, lotion, or emulsion. The composition may be formulated for transmucosal, transepithelial, transendothelial, or transdermal administration. One example of transdermal formulation is a patch. The composition may further comprise a chemical penetration enhancer, a membrane permeability agent, a membrane transport agent, a preservative, a surfactant, or a stabilizer, as these terms are known to those of skill in the art.

In one topical embodiment, the present invention can utilize a patch. A transdermal or "skin" patch is a medicated adhesive patch that is placed on the skin to deliver a time released dose of medication through the skin and into the bloodstream. A wide variety of pharmaceuticals can be delivered by transdermal patches. The first commercially available prescription patch was approved by the U.S. Food and Drug Administration in December 1979, which administered scopolamine for motion sickness.

The main components to a transdermal patch are (a) a liner to protect the patch during storage (removed prior to use); (b) the active agent; (c) an adhesive that serves to adhere the components of the patch together along with adhering the patch to the skin; (d) a membrane to control the release of the drug from the reservoir and multi-layer patches; and (e) a backing that protects the patch from the outer environment.

There are four main types of transdermal patches. Single-layer Drug-in-Adhesive patches have an adhesive layer that also contains the agent. In this type of patch the adhesive layer not only serves to adhere the various layers together, along with the entire system to the skin, but is also responsible for the releasing of the drug. The adhesive layer is surrounded by a temporary liner and a backing. Multi-layer Drug-in-Adhesive patches are similar to the single-layer system in that both adhesive layers are also responsible for the releasing of the drug. The multi-layer system is different however that it adds another layer of drug-in-adhesive, usually separated by a membrane (but not in all cases). This patch also has a temporary liner-layer and a permanent backing. Reservoir patches are unlike the Single-layer and Multi-layer Drug-in-Adhesive systems in that the reservoir transdermal system has a separate drug layer. The drug layer is a liquid compartment containing a drug solution or suspension separated by the adhesive layer. This patch is also backed by the backing layer. In this type of system the rate of release is zero order. Matrix patches have a drug layer of a semisolid matrix containing a drug solution or suspension. The adhesive layer in this patch surrounds the drug layer partially overlaying it.

In another form of treatment, a topical application of an $AT_2$ receptor antagonist is targeted at a natural body cavity such as the mouth, pharynx, esophagus, larynx, trachea, pleural cavity, peritoneal cavity, or hollow organ cavities including the bladder, colon or other visceral organs. A variety of methods may be employed to affect the topical application into these visceral organs or cavity surfaces. For example, the pharynx may be affected by simply oral swishing and gargling with solutions comprising an $AT_2$ receptor antagonist.

In particular embodiments, the composition is administered to a subject using a drug delivery device. Any drug delivery device is contemplated for use in delivering a pharmaceutically effective amount of an $AT_2$ receptor antagonist.

In certain embodiments, it may be desirable to provide a continuous supply of a pharmaceutical composition to the patient. This could be accomplished by catheterization, followed by continuous administration of the therapeutic agent. The administration could be intra-operative or post-operative.

In other embodiments, one may use eye or ear drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Without further description, one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Restoration of Sensory and Motor Nerve Conduction in Diabetic Rats

Methods: Diabetes was induced in mature (19 week old) male Sprague-Dawley by a single STZ injection (40-45 mg/kg i.p.). The diabetic state was monitored weekly using commercially available test strips for blood (tail vein) and urine glucose levels. Body weight was also monitored daily. The criteria for the diabetic state were: blood glucose>19.9 mM, glycosuria, and no evidence of body weight gain. The duration of diabetes was 8 weeks, and treatment was given for the last 2 weeks with the sodium salt of Compound 1 (1.048 mg/kg dissolved in water, daily by gavage).

In final experiments, rats were anaesthetized with thiobutabarbital (50-100 mg kg-1 i.p.) The trachea was cannulated for artificial respiration. The level of anaesthesia was monitored by observing any reaction of blood pressure to manipulation, supplementary thiobutabarbital anaesthetic being given as necessary. As described in detail by Cameron et al., (Q. J. Expt Physiol, 74; 917-926, 1989 and Diabetes, 40:532-539, 1991), the sciatic nerve was exposed between the sciatic notch and knee. Bipolar stimulating electrodes were placed close to the nerve at the notch and knee. A concentric bipolar electrode was inserted into tibialis anterior muscle to monitor evoked electromyographic (EMG) activity. Potentials evoked from each stimulating site were averaged 8 times. Motor nerve conduction velocity (NCV) was calculated by dividing the distance between stimulating electrodes by the average latency difference between the onsets of EMG potentials evoked from the 2 sites. Nerve temperature was monitored using a thermocouple probe, and maintained in the range 36-38° C. by radiant heat. Body temperature was also maintained around 37° C. using a heated blanket.

Sensory NCV was measured for sensory saphenous nerve between groin and mid-calf in a similar fashion, except that direct nerve evoked potentials were recorded at the ankle using a unipolar platinum hook electrode.

Reference values for comparison of the NCV data following treatment with the sodium salt of Compound 1 were obtained from nondiabetic control and 8 week diabetic control rats during the course of these studies.

Results: Data for individual diabetic rats treated orally with the sodium salt of Compound 1 are given in Table 1. All animals showed a modest weight loss over the 8 week period, entirely in keeping with the characteristics of the diabetic model. At the end of the experimental period, animals remained in good condition and behaviourally alert, were not cachexic and had good final body weights. Non-fasted plasma glucose measurements confirmed the diabetic state.

Group mean NCV data are also shown in FIG. 1. For sciatic motor NCV, the approximately 20% reduction with diabetes shown by the reference groups was largely corrected by Compound 1 treatment; this represents a 92.6±5.4% reversal of the diabetic deficit. Statistically (one way ANOVA followed by Bonferroni test), the group treated with Compound 1 data were not significantly different from those of the nondiabetic control group, and markedly improved (p<0.001) compared to untreated diabetes. A similar trend was seen for saphenous sensory NCV (FIG. 1). The 17% diabetic deficit for the reference groups was 99.1±5.0% corrected (p<0.001) by oral treatment with the sodium salt of Compound 1.

TABLE 1

Data for individual 1.048 mg/kg Compound 1 sodium salt treated diabetic rats

| Rat | Start weight (g) | End weight (g) | Blood glucose (mM) | Motor NCV (m/s) | Sensory NCV (m/s) |
|---|---|---|---|---|---|
| 1 | 462 | 360 | 33.0 | 69.57 | 60.98 |
| 2 | 456 | 425 | 28.1 | 63.81 | 60.74 |
| 3 | 472 | 429 | 26.2 | 62.87 | 62.50 |
| 4 | 462 | 380 | 55.6 | 62.30 | 60.63 |
| 5 | 479 | 389 | 32.4 | 62.84 | 62.50 |
| 6 | 433 | 393 | 49.6 | 62.50 | 60.41 |
| 7 | 468 | 390 | 27.8 | 63.90 | 62.50 |
| 8 | 459 | 353 | 28.2 | 62.69 | 60.71 |
| 9 | 460 | 366 | 38.6 | 64.95 | 57.57 |
| 10 | 464 | 418 | 36.2 | 61.75 | 62.50 |
| Mean | 462 | 390 | 35.57 | 63.72 | 61.10 |
| SEM | 4 | 9 | 3.30 | 0.75 | 0.51 |

Reference values:
Nondiabetic controls (n = 10); motor NCV 64.7 ± 0.7 m/s, sensory NCV 61.0 ± 0.6 m/s.
Diabetic controls (n = 10); motor NCV 50.2 ± 0.5 m/s, sensory NCV 51.8 ± 0.7 m/s.

Example 2

Dose Response for Compound 1 Sodium Salt in Restoration of Sensory and Motor Nerve Conduction in Diabetic Rats Methods: Diabetes was induced in mature (19 week old) male Sprague-Dawley by a single STZ injection (40-45 mg/kg i.p.). The diabetic state was monitored weekly using commercially available test strips for blood (tail vein) and urine glucose levels. Body weight was also be monitored daily. The criteria for the diabetic state were: blood glucose>19.9 mM, glycosuria, and no evidence of body weight gain. The duration of diabetes was 8 weeks, and treatment was given for the last 2 weeks with Compound 1 (groups of 10 diabetic rats given the sodium salt of Compound 1 at doses of 0.1048, 0.0349 or 0.01048 mg/kg dissolved in water, daily by gavage).

In final experiments, rats were anaesthetized with thiobutabarbital (50-100 mg kg-1 i.p.) The trachea was cannulated for artificial respiration. The level of anaesthesia was monitored by observing any reaction of blood pressure to manipulation, supplementary thiobutabarbital anaesthetic being given as necessary. The sciatic nerve was exposed between the sciatic notch and knee. Bipolar stimulating electrodes were placed close to the nerve at the notch and knee. A concentric bipolar electrode was inserted into tibialis anterior muscle to monitor evoked electromyographic (EMG) activity. Potentials evoked from each stimulating site were averaged 0.8 times. Motor NCV was calculated by dividing the distance between stimulating electrodes by the average latency difference between the onsets of EMG potentials evoked from the 2 sites. Nerve temperature was monitored using a thermocouple probe, and maintained in the range 36-38° C. by radiant heat. Body temperature was also maintained around 37° C. using a heated blanket. Sensory NCV was measured for sensory saphenous nerve between groin and mid-calf in a similar fashion, except that direct nerve evoked potentials were recorded at the ankle using a unipolar platinum hook electrode. Reference values for comparison of the NCV data were obtained from nondiabetic control and 8 week diabetic control rats.

Results: Data for individual diabetic rats treated orally with the sodium salt of Compound 1 at the different doses are given in Tables 2 through 4 and the previously obtained data for 1.048 mg/kg are shown in Table 1. All animals showed a modest weight loss over the 8 week period, entirely in keeping with the characteristics of the diabetic model. At the end of the experimental period, animals remained in good condition and behaviourally alert, were not cachexic and had good final body weights. Non-fasted plasma glucose measurements confirmed the diabetic state.

Figure 2:
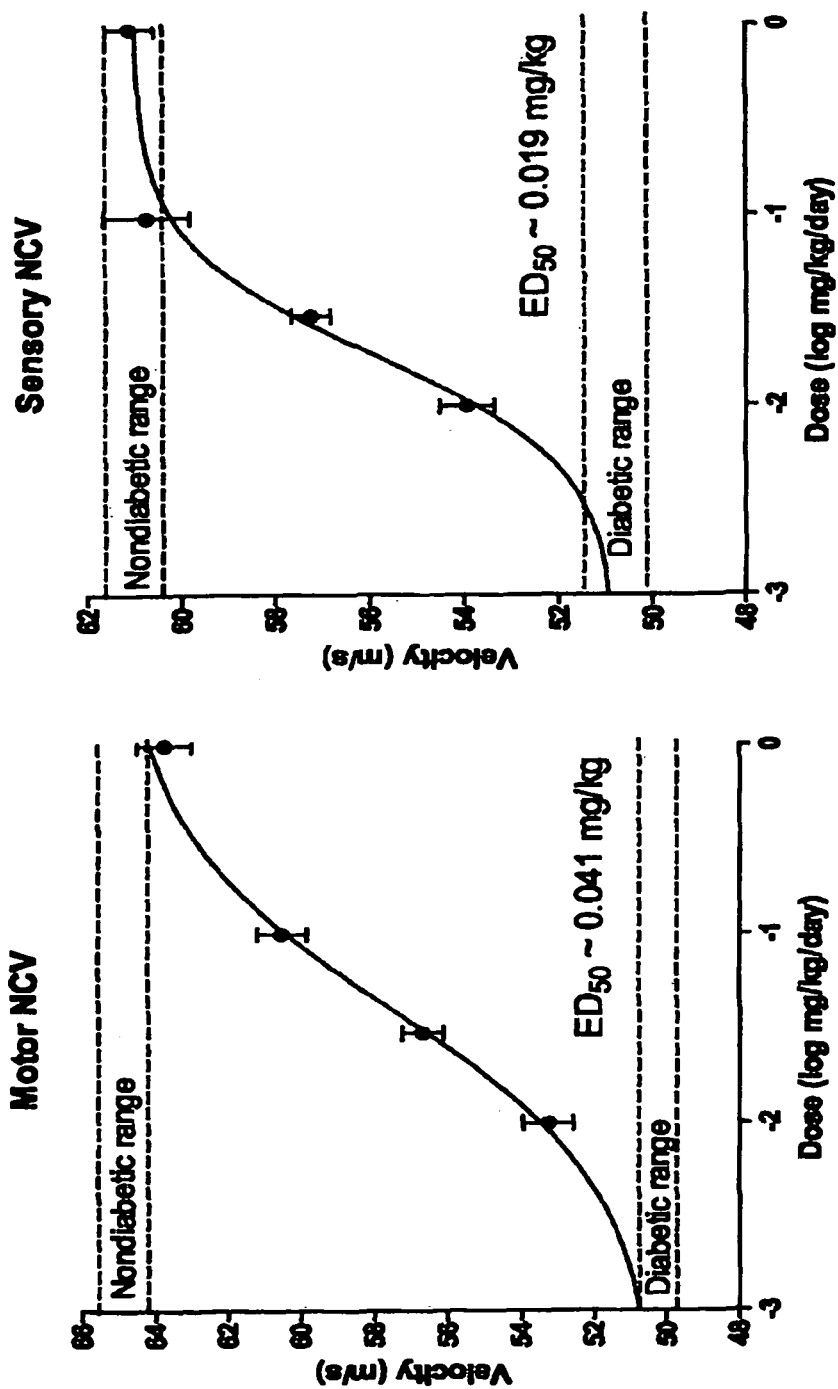
FIG. 2 is a graphical representation of the dose response curve for correction of motor and sensory nerve conduction velocity deficits in diabetic rats by treatment with Compound 1 at oral dose levels≤1.043 mg/kg. Data are mean±SEM, curves are best fitting sigmoids.

Dose-response curves for motor and sensory NCV are plotted in FIG. 2, along with best fit sigmoid curves for estimation of $ED_{50}$ values. For sciatic motor NCV, the approximately 20% reduction with diabetes shown by the reference groups was dose-dependently corrected by oral treatment with the sodium salt of Compound 1, with an $ED_{50}$ of 0.044 mg/kg. A similar trend was seen for saphenous sensory NCV, the $ED_{50}$ being 0.02 mg/kg.

TABLE 2

Data for individual 0.1048 mg/kg Compound 1 sodium salt treated diabetic rats

| Rat | Start weight (g) | End weight (g) | Blood glucose (mM) | Motor NCV (m/s) | Sensory NCV (m/s) |
|---|---|---|---|---|---|
| 1 | 491 | 374 | 30.0 | 60.00 | 58.33 |
| 2 | 491 | 440 | 52.2 | 58.33 | 55.83 |
| 3 | 484 | 398 | 30.3 | 59.13 | 61.11 |
| 4 | 510 | 363 | 31.0 | 61.48 | 62.96 |
| 5 | 458 | 298 | 27.5 | 60.00 | 61.22 |
| 6 | 459 | 315 | 27.6 | 58.62 | 56.67 |
| 7 | 463 | 357 | 32.0 | 63.63 | 63.16 |
| 8 | 468 | 346 | 32.8 | 64.15 | 62.50 |
| 9 | 456 | 392 | 34.2 | 59.02 | 63.04 |
| 10 | 493 | 405 | 31.8 | 60.78 | 62.50 |
| Mean | 477 | 369 | 32.94 | 60.51 | 60.73 |
| SEM | 6 | 14 | 2.36 | 0.68 | 0.92 |

TABLE 3

Data for individual 0.0349 mg/kg Compound 1 sodium salt treated diabetic rats

| Rat | Start weight (g) | End weight (g) | Blood glucose (mM) | Motor NCV (m/s) | Sensory NCV (m/s) |
|---|---|---|---|---|---|
| 1 | 500 | 368 | 32.2 | 54.55 | 57.72 |
| 2 | 500 | 368 | 28.7 | 56.06 | 56.72 |
| 3 | 530 | 369 | 34.6 | 56.15 | 57.43 |
| 4 | 483 | 427 | 30.3 | 57.38 | 57.94 |
| 5 | 500 | 400 | 37.8 | 56.90 | 55.60 |
| 6 | 463 | 396 | 34.6 | 57.89 | 59.95 |
| 7 | 467 | 332 | 30.3 | 59.32 | 56.00 |

TABLE 3-continued

Data for individual 0.0349 mg/kg Compound 1 sodium salt treated diabetic rats

| Rat | Start weight (g) | End weight (g) | Blood glucose (mM) | Motor NCV (m/s) | Sensory NCV (m/s) |
|---|---|---|---|---|---|
| 8 | 463 | 307 | 30.4 | 56.67 | 57.50 |
| 9 | 485 | 277 | 39.6 | 53.68 | 55.93 |
| 10 | 462 | 327 | 27.8 | 58.18 | 57.73 |
| Mean | 485 | 357 | 32.63 | 56.68 | 57.25 |
| SEM | 7 | 15 | 1.30 | 0.56 | 0.42 |

TABLE 4

Data for individual 0.01048 mg/kg Compound 1 sodium salt treated diabetic rats

| Rat | Start weight (g) | End weight (g) | Blood glucose (mM) | Motor NCV (m/s) | Sensory NCV (m/s) |
|---|---|---|---|---|---|
| 1 | 494 | 386 | 28.4 | 50.70 | 53.85 |
| 2 | 463 | 312 | 37.2 | 52.38 | 53.19 |
| 3 | 501 | 374 | 26.7 | 54.92 | 55.47 |
| 4 | 535 | 436 | 34.2 | 55.17 | 56.07 |
| 5 | 523 | 346 | 37.6 | 54.10 | 51.59 |
| 6 | 567 | 438 | 39.8 | 50.78 | 54.39 |
| 7 | 516 | 349 | 38.4 | 54.03 | 55.30 |
| 8 | 452 | 329 | 33.2 | 51.60 | 51.82 |
| 9 | 466 | 364 | 27.9 | 51.96 | 51.85 |
| 10 | 483 | 385 | 32.4 | 56.90 | 55.81 |
| Mean | 500 | 372 | 33.58 | 53.25 | 53.93 |
| SEM | 12 | 14 | 1.57 | 0.69 | 0.58 |

Example 3

Selectivity of Compound 1 for the $AT_2$ Receptor

Selectivity of Compound 1 for the $AT_2$ receptor was determined in an in vitro human $AT_1$ and $AT_2$ receptor binding assay.

| Methods: General Procedures | | | |
|---|---|---|---|
| Assay | Origin | Reference Compound | Bibliography |
| $AT_1$ (h) | human recombinant (CHO cells) | saralasin | Bergsma et al. (1992); Biochem. Biophys. Res. Commun. 183: 989-995 |
| $AT_2$ (h) | human recombinant (Hela cells) | saralasin | Tsuzuki et al. (1994), Biochem. Biophys. Res. Commun. 200: 1449-1454 |

| Experimental Conditions | | | | | |
|---|---|---|---|---|---|
| Assay | Ligand | Conc. | Non Specific | Incubation | Method of Detection |
| $AT_1$ (h) | [$^{125}$I][Sar$^1$, Ile$^8$]-AT II | 0.05 nM | angiotensin II (10 μM) | 60 min./37° C. | Scintillation counting |
| $AT_2$ (h) | [$^{125}$I]CGP 42112A | 0.05 nM | angiotensin II (1 μM) | 180 min./37° C. | Scintillation counting |

Analysis and Expression of Results

The specific ligand binding to the receptors is defined as the difference between the total binding and the nonspecific binding determined in the presence of an excess of unlabelled ligand.

The results are expressed as a percent of control specific binding obtained in the presence of Compound 1. The $IC_{50}$ values (concentration causing a half-maximal inhibition of control specific binding) and Hill coefficients ($n_H$) were determined by non-linear regression analysis of the competition curves using Hill equation curve fitting. The inhibition constants (Ki) were calculated from the Cheng Prusoff equation ($Ki=IC_{50}/(1+(L/K_D))$, where L=concentration of radioligand in the assay, and $K_D$=affinity of the radioligand for the receptor).

Results: The $IC_{50}$ and Ki values determined for Compound 1 are indicated in Table 5.

TABLE 5

| $IC_{50}$ Determination: Summary Results | | | | | |
|---|---|---|---|---|---|
| Assay | Compound | $IC_{50}$ (M) | $K_i$ (M) | $n_H$ | Flags |
| $AT_1$ (h) | Compound 1 | | | | N.C. |
| $AT_2$ (h) | Compound 1 | 3.9E−08 | 5.4E−09 | 1.3 | |

N.C.: Not calculable. $IC_{50}$ value is not calculable because of less than 25% inhibition at the highest tested concentration.

Example 4

Treatment of a Subject to Increase NCV

A subject suffering from impaired NCV is identified by symptomology and/or measurement of NCV under standard and accepted protocols. In the present example, a subject presents suffering from numbness or tingling in one or more limbs. Motor and sensory NCV studies are performed with accompanying F-waves and H-reflex studies. NCV measurement or other diagnosis indicates that NCV is impaired.

The subject is administered an initial dose equivalent to a daily dose of 0.1 mg/kg of S-2-(diphenylacetyl)-5-benzyloxy-6-methoxy-1,2,3,4-tetrahydroisoquinoline-3-carboxylic acid or salt thereof providing the equivalent dose for an initial regime of from 1 to 14 days. At the conclusion of the initial regime, assessment of NCV or symptoms is repeated. Measurable improvement in NCV or improvement in symptoms indicates that treatment is effective. If no improvement in NCV or symptoms is detected, the daily dose is increased, for example to 0.2 mg/kg. After a subsequent and suitable time of treatment, measurement of NCV or symptoms is repeated. Measurable improvement in NCV or improvement in symptoms indicates that treatment is effective.

If no improvement in NCV or symptoms is detected, then a stepwise process of modulating dose followed by measurement of NCV of symptoms is repeated until improvement is satisfactory. Further titration of the daily does to a minimum sufficient to effect a desired improvement is achieved by step-wise decrease of the daily dose to a minimum daily dose required for effective treatment in the subject.

Example 5

Time Course of Treatment in Restoration of Sensory and Motor Nerve Conduction in Rats Diabetes was induced in mature (19 week old) male Sprague-Dawley by a single STZ injection (40-45 mg/kg i.p.). The diabetic state was monitored weekly using commercially available test strips for blood (tail vein) and urine glucose levels. Body weight was also monitored daily. The criteria for the diabetic state were: blood glucose>19.9 mM, glycosuria, and no evidence of body weight gain. The duration of diabetes was 8 weeks, and treatment with the sodium salt of Compound 1 was given for either 1, 3, 7 or 28 days. For each treatment period, separate groups of 10 diabetic rats were given the sodium salt of Compound 1 at a dose level of 1.048 mg/kg dissolved in water, daily by oral gavage.

Tactile allodynia thresholds for the foot were measured by an electronic von Frey hair apparatus. Latencies for foot withdrawal reflexes to noxious thermal stimulation were estimated by the Hargreaves plantar test (Hargreaves K, Dubner R, Brown F, Flores C, Joris J. A new and sensitive method for measuring thermal nociception in cutaneous hypeialgesia. Pain 1988; 32: 77-88). All tests were carried out using commercially available equipment (Ugo-Basile, Comerio, Italy). Measurements were made in a constant temperature room at the same time each day, and rats were given a 3-day period for familiarization with handling, the environment, equipment, and experimental procedure.

Tactile allodynia was estimated on two separate occasions; once on a day before treatment was initiated, and then on the day immediately following the last day of the treatment period. Stimulus intensity started at 2 g and if a withdrawal response to stimulation did not occur within 8 s, the stimulus was increased by a 0.2 log unit increment and reapplied. When a positive withdrawal response was obtained, stimulus intensity was lowered by 0.2 log units. Thus, stimulus intensity tracked the threshold, and a run of 6 near-threshold responses was used to estimate the 50% threshold value using lookup tables (Chaplan S R, Bach F W, Pogrel J W, Chung J M, Yaksh T L. Quantitative assessment of tactile allodynia in the rat paw. J Neurosci Meth 1994; 53: 55-63). Measurements were made for both feet, the average being taken to represent the 50% threshold for an individual rat.

In a similar way to the assessment of tactile allodynia, thermal sensitivity was also measured on 2 separate occasions, before and after treatment. Rats were placed in the thermal testing apparatus. After 30 min acclimatization, a constant power infrared stimulus was focused onto the sole of the foot and the latency for reflex foot withdrawal recorded via a photoelectric monitor. For each session, 8 measurements were obtained, 4 from each foot, the average being taken to represent foot withdrawal latency to thermal stimulation.

In final experiments, rats were anaesthetized with thiobutabarbital (50-100 mg kg-1 i.p.) The trachea was cannulated for artificial respiration. The level of anaesthesia was monitored by observing any reaction of blood pressure to manipulation, supplementary thiobutabarbital anaesthetic being given as necessary. The sciatic nerve was exposed between the sciatic notch and knee. Bipolar stimulating electrodes were placed close to the nerve at the notch and knee. A concentric bipolar electrode was inserted into tibialis anterior muscle to monitor evoked electromyographic (EMG) activity. Potentials evoked from each stimulating site were averaged 8 times. Motor NCV was calculated by dividing the distance between stimulating electrodes by the average latency difference between the onsets of EMG potentials evoked from the 2 sites. Nerve temperature was monitored using a thermocouple probe, and maintained in the range 36-38° C. by radiant heat. Body temperature was also maintained around 37° C. using a heated blanket. Sensory NCV was measured for sensory saphenous nerve between groin and mid-calf in a similar fashion, except that direct nerve evoked potentials were recorded at the ankle using a unipolar platinum hook electrode.

For the short treatment (1, 3 and 7 days) duration groups, animals were studied in batches of 3 or 4, staggered in time until the group numbers were achieved (n=10). This was done in order to keep the timing of measurements well synchronized with drug dosage, given that a set of measurements on each rat can take a significant time. For these groups of rats, all measurements were completed within 22 to 26 hours of the last drug gavage.

Data were analysed using GraphPad Prism 5 software. They were subjected to one-way ANOVA followed by Bonferroni post hoc multiple comparison tests to establish between-group differences. In addition, for the behavioural estimates where before and after drug administration measurements were made, results were analysed using paired Student's t-tests.

Results: Timecourse data are compared with nondiabetic and 8-week diabetic control data obtained in the previous study (Example 1). Data from a 14-day treatment group from Example 1 are also included in some of the graphs.

Figure 3:
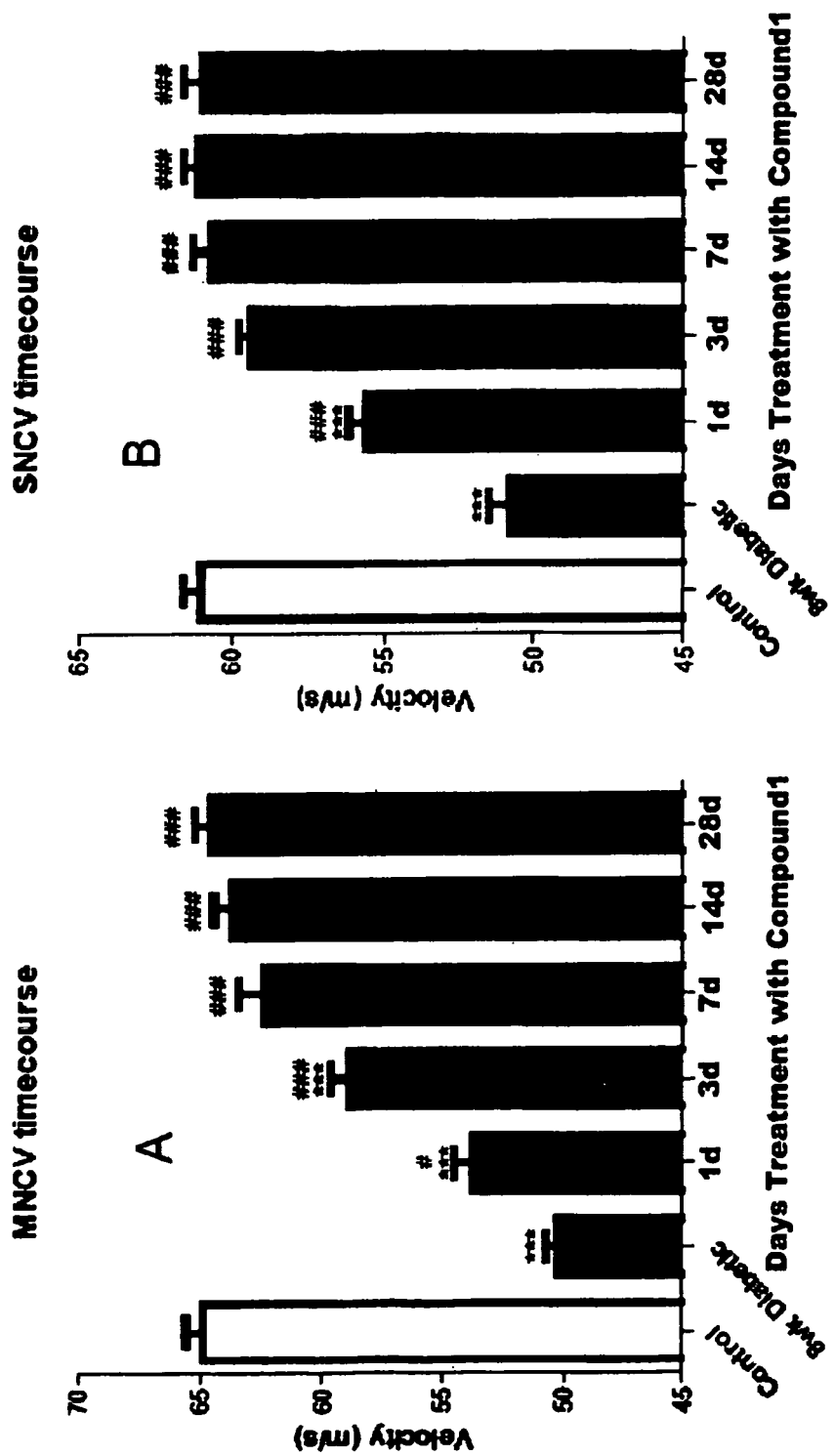
FIG. 3 is a graphical representation of the effects of diabetes and treatment with Compound 1 at an oral dose level of 1.043 mg/kg on (A) sciatic motor nerve conduction velocity (MNCV) and (B) saphenous sensory nerve conduction velocity (SNCV) for 1, 3, 7 14 and 28 days duration. Data are mean+SEM. *** $P<0.001$, vs nondiabetic control group; ###, # $P<0.001$, $<0.05$ treatment effect vs diabetic control group.

Motor and sensory NCV timecourses: For both motor and sensory NCV there were statistically significant effects of as little as 1 day of treatment with the sodium salt of Compound 1 (FIG. 3). Correction of NCV deficits appeared to be somewhat more rapid for sensory nerves. Statistically, motor NCV was within the nondiabetic range after 7 days treatment, sensory NCV after 3 days. Data for the 28-day treatment group were entirely comparable with the previously obtained 14-day data. Thus, over this time there was no evidence of a waning of the drug effects.

Figure 4:
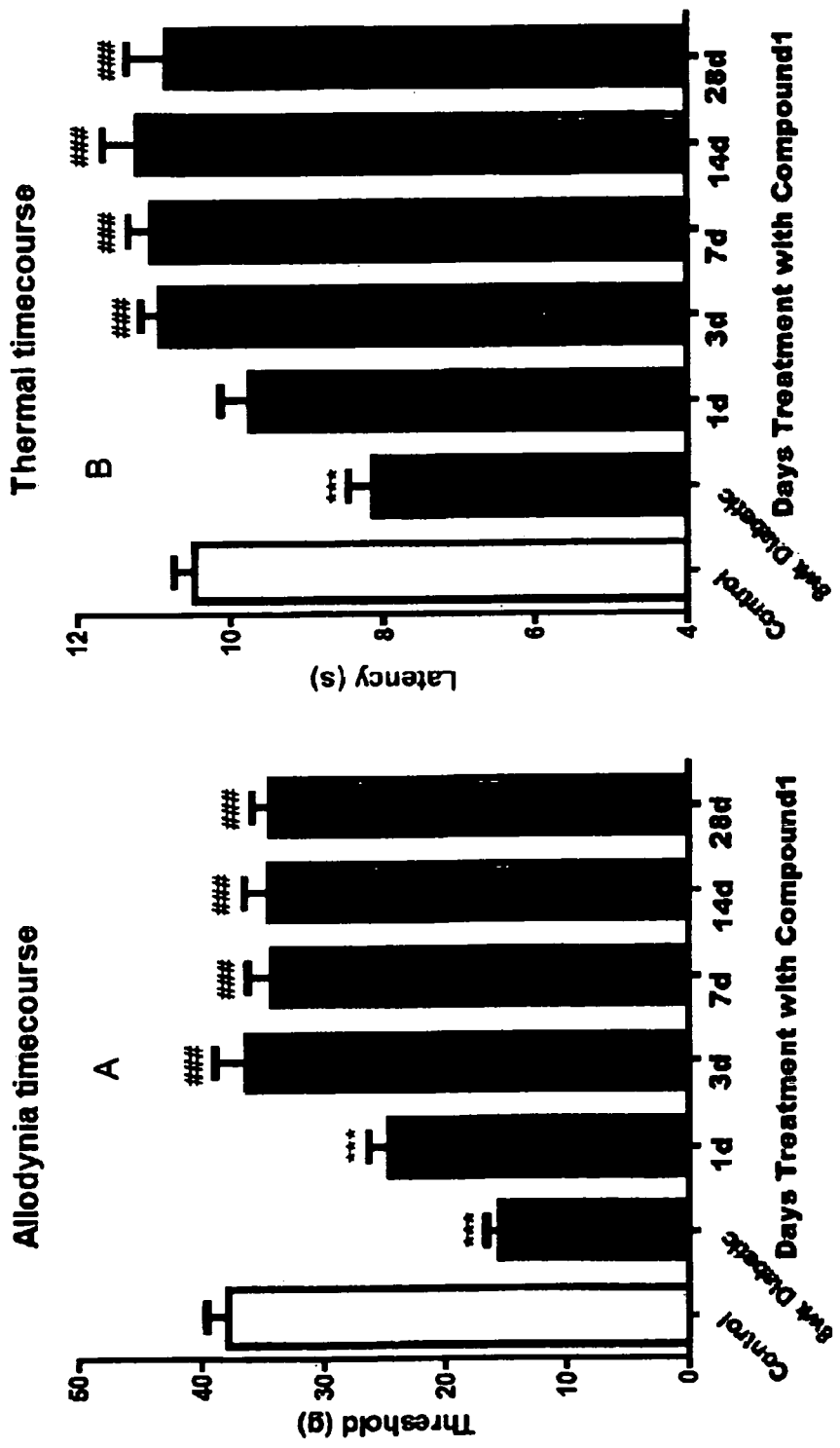
FIG. 4 is a graphical representation of the effects of diabetes and Compound 1 at an oral dose level of 1.043 mg/kg on behavioural measures of (A) tactile allodynia and (B) thermal hyperalgesia for 1, 3, 7 14 and 28 days duration. Data are mean+SEM. *** $P<0.001$, vs nondiabetic control group; ###, $P<0.001$ treatment effect vs diabetic control group.
Figure 5:
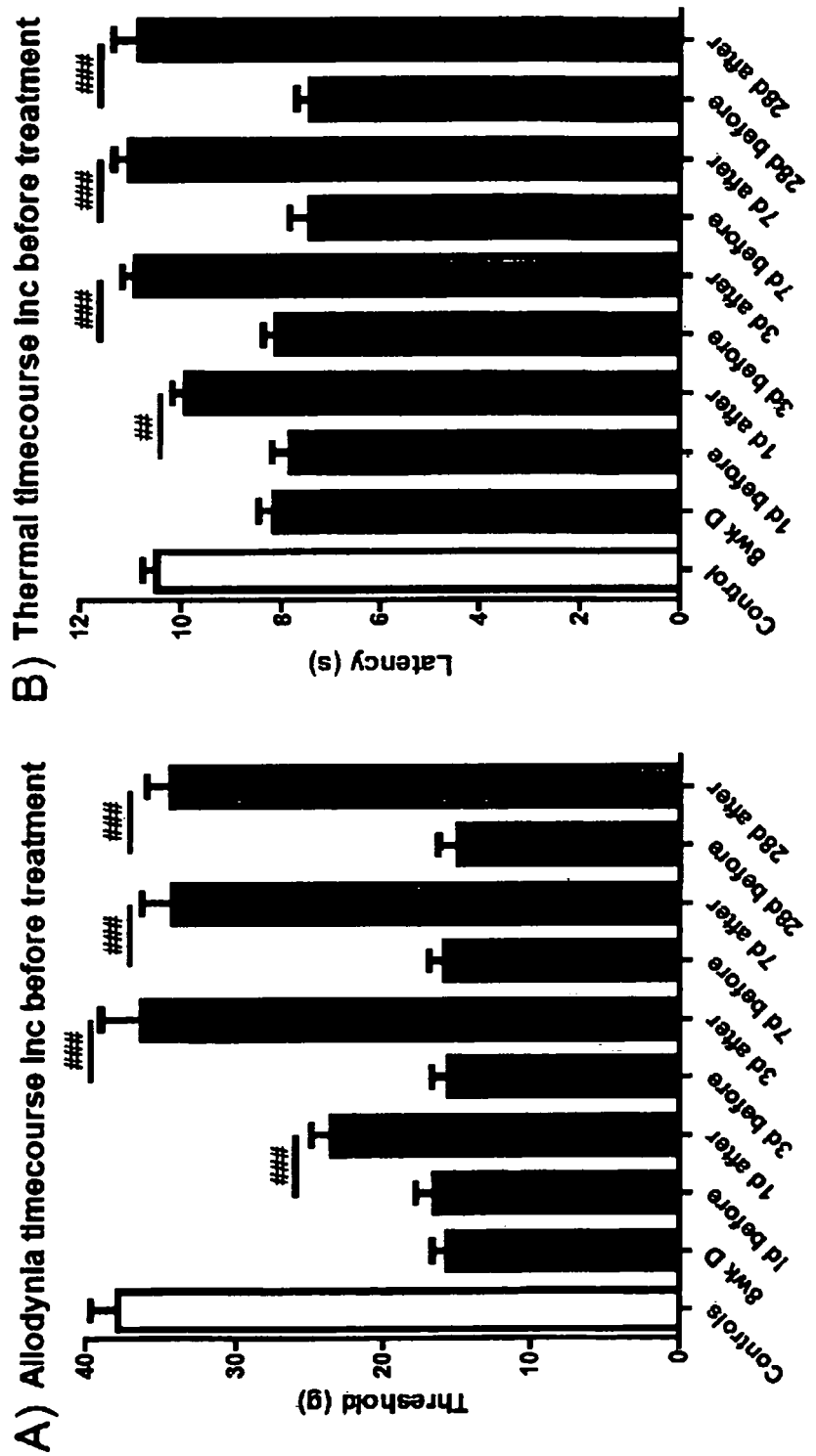
FIG. 5 is a graphical representation of the effects of diabetes and treatment with Compound 1 at an oral dose level of 1.043 mg/kg on behavioural measures of (A) tactile allodynia and (B) thermal hyperalgesia showing before drug and after drug treatment values, along with paired-t statistics. Data are mean+SEM. ###, ## $P<0.001$, $<0.01$ treatment effect vs before (paired Student's t-test).

For both tactile allodynia and thermal hyperalgesia, the timecourse was similar to sensory NCV, full correction being achieved after 3 days of treatment with the sodium salt of Compound 1 (FIG. 4). Data are also plotted as a histogram (without the 14-day group) showing before drug and after drug treatment values, along with paired-t statistics (FIG. 5). This data shows that the before results are similar for the different groups, showing that the diabetic effect is stable over time (previous work also showed that this was maintained for at least 6 months of diabetes). The use of paired Student's t-statistic analysis also highlights the significant, albeit partial, effects of only 1 day of treatment. Data for individual animals are plotted in FIG. 4, before and after drug. In all individual rats (except for one animal for 1-day treatment thermal measurement), there was an improvement of responses.

Overall, treatment with the sodium salt of Compound 1 corrected large myelinated fibre motor and sensory NCV deficits in experimental diabetes. There was a significant but partial effect 1 day after a single administration of the drug. Normalization was achieved after 3-7 days treatment. Sensory NCV seemed to be somewhat more amenable to treatment than motor NCV in that responses were normalized earlier than motor NCV. Tactile allodynia and thermal hyperalgesia were also rapidly corrected, with a timecourse similar to that for sensory NCV. Responses to Compound 1 were maintained over 28 days treatment.

All of the compositions or methods disclosed and claimed herein can be made and executed without undue experimentation in light of the present disclosure. While the compositions and methods of this invention have been described in terms of preferred embodiments, it will be apparent to those of skill in the art that variations may be applied to the compositions or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All publications and patent applications cited in this specification are herein incorporated by reference as if each individual publication or patent application were specifically and individually indicated to be incorporated by reference.

REFERENCES

The following references, and references cited hereinabove, to the extent that they provide exemplary procedural or other details supplementary to those set forth herein, are specifically incorporated herein by reference.

U.S. Patent Application Publication No. 20090117267
U.S. Pat. No. 4,291,705,
U.S. Pat. No. 4,807,643
U.S. Pat. No. 7,628,761
WO 93/20816
WO 2006/066361
American Association of Neuromuscular & Electrdiagnostic Medicine (AANEM). "Proper performance and interpretation of electrodiagnostic studies." Muscle Nerve. March; 33(3):436-9, 2006.
American Medical Association. "Electrodiagnostic medicine listing of sensory, motor, and mixed nerves." Appendix J of Current Procedural Terminology (CPT) 4th edition (Oct. 30, 2007).
Bergsma et al., Biochem. Biophys. Res. Commun. 183: 989-995, 1992.
Blankley et al., J. Med. Chem. 34:3248-3260, 1991.
Cameron et al., Q. J. Expt Physiol, 74; 917-926, 1989.
Cameron et al., Diabetes, 40:532-539, 1991.
Chaplan, S. R. et al., J Neurosci Meth, 53: 55-63, 1994.
Chiu, A. T. et al., Biochem. Biophys. Res. Commun. 165:196-203, 1989.
Hargreaves, K. et al., Pain, 32: 77-88, 1988.
Klutchko et al., Bioorganic & Medicinal Chemistry Letters 4(1):57-62, 1994.
Remington's Pharmaceutical Sciences, 18th Ed. Mack Printing Company, 1990.
Tsuzuki et al., Biochem. Biophys. Res. Common. 200: 1449-1454, 1994.
VanAtten et al. J. Med. Chem. 36(25):3985-3992, 1993.

What is claimed is:

1. A method for treating impaired nerve conduction velocity (NCV) in a subject in need of improved nerve conduction velocity, the method comprising providing to said subject a composition comprising a compound of formula (II) or formula (III):

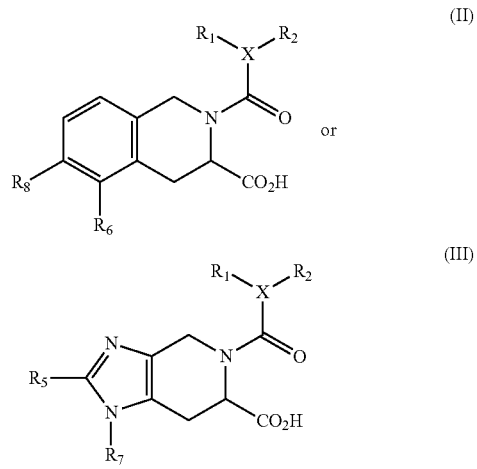

wherein:
$R_1$ and $R_2$ are independently selected from hydrogen, phenyl, benzyl, $C_1$-$C_6$ alkyl, $C_3$-$C_6$ cycloalkyl and heteroaryl, provided that $R_1$ and $R_2$ are not both hydrogen;
X is selected from CH, N, O and S provided that when X is O or S, one of $R_1$ and $R_2$ is absent;
$R_5$ is selected from hydrogen, $C_1$-$C_6$ alkyl, phenyl and $C_1$-$C_6$ alkoxy,
$R_6$ and $R_8$ are independently selected from hydrogen, $C_1$-$C_6$ alkyl, $C_1$-$C_6$ alkoxy, phenyl, benzyl, phenoxy, benzyloxy, benzylamino, biphenyl, biphenyloxy, naphthyl and naphthyloxy; provided that $R_6$ and $R_8$ are not both hydrogen; and
$R_7$ is selected from phenyl, benzyl, biphenyl, biphenylmethyl, naphthyl and naphthylmethyl;
wherein each alkyl, alkoxy, aryl, cycloalkyl, aryloxy, arylalkyl, arylalkyloxy and heteroaryl group is optionally substituted,
or a pharmaceutically acceptable salt thereof;
in an amount effective to improve nerve conduction velocity in said subject.

2. The method according to claim 1 wherein $R_1$ and $R_2$ are both phenyl, and pharmaceutically acceptable salts thereof.

3. The method according to claim 1 wherein X is CH, and pharmaceutically acceptable salts thereof.

4. The method according to claim 1 wherein $R_6$ is optionally substituted phenoxy or optionally substituted benzyloxy, and pharmaceutically acceptable salts thereof.

5. The method according to claim 4 wherein $R_6$ is benzyloxy, and pharmaceutically acceptable salts thereof.

6. The method according to claim 1 wherein $R_8$ is hydrogen, optionally substituted $C_1$-$C_6$ alkyl, or optionally substituted $C_1$-$C_6$ alkoxy, and pharmaceutically acceptable salts thereof.

7. The method according to claim 6 wherein $R_8$ is methoxy, and pharmaceutically acceptable salts thereof.

8. The method according to claim 1 wherein $R_5$ is hydrogen, and pharmaceutically acceptable salts thereof.

9. The method according to claim 1 wherein $R_7$ is optionally substituted benzyl, optionally substituted biphenylmethyl and optionally substituted naphthylmethyl, and pharmaceutically acceptable salts thereof.

10. The method according to claim 8 wherein $R_7$ is optionally substituted benzyl, and pharmaceutically acceptable salts thereof.

11. The method of claim 1, wherein the compound is a compound of formula (II):

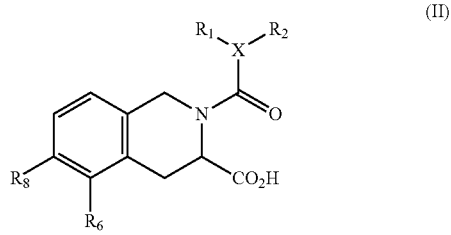

(II)

and pharmaceutically acceptable salts thereof.

12. The method of claim 11, wherein the compound of formula (II) is a compound of formula (IIA):

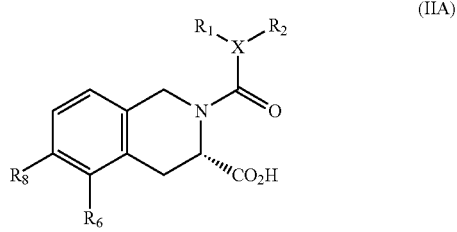

(IIA)

and pharmaceutically acceptable salts thereof.

13. The method of claim 11, wherein the compound of formula (II) is 2-(diphenylacetyl)-5-benzyloxy-6-methoxy-1,2,3,4-tetrahydroisoquinoline-3-carboxylic acid, and pharmaceutically acceptable salts thereof.

14. The method of claim 12, wherein the compound of formula (IIA) is S-2-(diphenylacetyl)-5-benzyloxy-6-methoxy-1,2,3,4-tetrahydroisoquinoline-3-carboxylic acid (Compound 1), and pharmaceutically acceptable salts thereof.

15. The method of claim 1, wherein the compound is a compound of formula (III):

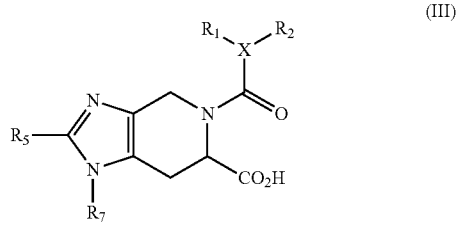

(III)

and pharmaceutically acceptable salts thereof.

16. The method of claim 15, wherein the compound of formula (III) is a compound of formula (IIIA):

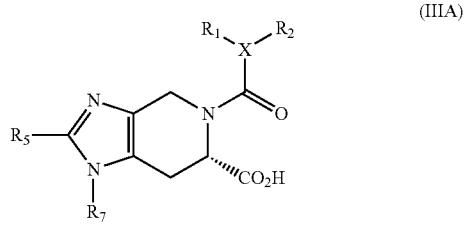

(IIIA)

and pharmaceutically acceptable salts thereof.

17. The method of claim 15, wherein the compound of formula (III) is 1-[[4-(dimethylamino)-3-methylphenyl]methyl]-5-diphenylacetyl-4,5,6,7-tetrahydro-1H-imidazo-[4,5c]pyridine-6-carboxylic acid or 1-[[4-methoxy-3-methylphenyl]methyl]-5-diphenylacetyl-4,5,6,7-tetrahydro-1H-imidazo-[4,5c]pyridine-6-carboxylic acid, and pharmaceutically acceptable salts thereof.

18. The method of claim 16, wherein the compound of formula (IIIA) is S-1-[[4-(dimethylamino)-3-methylphenyl]methyl]-5-diphenylacetyl-4,5,6,7-tetrahydro-1H-imidazo-[4,5c]pyridine-6-carboxylic acid or S-1-[[4-methoxy-3-methylphenyl]-methyl]-5-diphenylacetyl-4,5,6,7-tetrahydro-1H-imidazo-[4,5c]pyridine-6-carboxylic acid, and pharmaceutically acceptable salts thereof.

19. The method according to claim 1 wherein said subject suffers from diminished reflex responses and altered peripheral sensation including paresthesia.

20. The method of claim 1, wherein said subject is diagnosed with a neuropathy.

21. The method of claim 20, wherein said subject has a diabetic neuropathy.

22. The method of claim 20, wherein said subject is being treated for an acquired neuropathy.

23. The method according to claim 1 wherein the improved nerve conduction velocity is reversing impaired nerve conduction velocity in said subject.

24. A method of reversing impaired neuronal conduction velocity in a subject in need of improved nerve conduction velocity comprising administering to said subject a compound of formula (II) or formula (III):

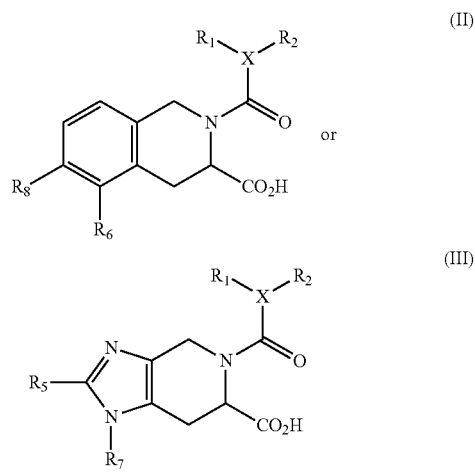

wherein:

$R_1$ and $R_2$ are independently selected from hydrogen, phenyl, benzyl, $C_1$-$C_6$ alkyl, $C_3$-$C_6$ cycloalkyl and heteroaryl, provided that $R_1$ and $R_2$ are not both hydrogen;

X is selected from CH, N, O and S provided that when X is O or S, one of $R_1$ and $R_2$ is absent;

$R_5$ is selected from hydrogen, $C_1$-$C_6$ alkyl, phenyl and $C_1$-$C_6$ alkoxy, $R_6$ and $R_8$ are independently selected from hydrogen, $C_1$-$C_6$ alkyl, $C_1$-$C_6$ alkoxy, phenyl, benzyl, phenoxy, benzyloxy, benzylamino, biphenyl, biphenyloxy, naphthyl and naphthyloxy; provided that $R_6$ and $R_8$ are not both hydrogen; and $R_7$ is selected from phenyl, benzyl, biphenyl, biphenylmethyl, naphthyl and naphthylmethyl;

wherein each alkyl, alkoxy, aryl, cycloalkyl, aryloxy, arylalkyl, arylalkyloxy and heteroaryl group is optionally substituted, or a pharmaceutically acceptable salt thereof;
in an amount effective to improve nerve conduction velocity in said subject.

\* \* \* \* \*

UNITED STATES PATENT AND TRADEMARK OFFICE
CERTIFICATE OF CORRECTION

| | |
|---|---|
| PATENT NO. | : 9,095,587 B2 |
| APPLICATION NO. | : 13/522228 |
| DATED | : August 4, 2015 |
| INVENTOR(S) | : Thomas David McCarthy and Andrew Rainsford Baker |

It is certified that error appears in the above-identified patent and that said Letters Patent is hereby corrected as shown below:

On the title page item 75 the spelling of the last name of the second inventor reading "Bakeb" should read --Baker--.

Signed and Sealed this
Sixteenth Day of February, 2016

Michelle K. Lee
*Director of the United States Patent and Trademark Office*